(12) United States Patent
Hirayama et al.

(10) Patent No.: US 8,214,053 B2
(45) Date of Patent: Jul. 3, 2012

(54) BODY HEATING DEVICE

(75) Inventors: Kotaro Hirayama, Kawasaki (JP);
Isamu Tomoda, Kawasaki (JP);
Shuichiro Miyata, Kawasaki (JP)

(73) Assignees: Nanotherapy Co., Ltd., Nagoya-Shi (JP); Dai-Ichi High Frequency Co., Ltd., Tokyo (JP)

( * ) Notice: Subject to any disclaimer, the term of this patent is extended or adjusted under 35 U.S.C. 154(b) by 1235 days.

(21) Appl. No.: 11/920,435

(22) PCT Filed: Aug. 29, 2006

(86) PCT No.: PCT/JP2006/316983
§ 371 (c)(1),
(2), (4) Date: Nov. 15, 2007

(87) PCT Pub. No.: WO2008/026254
PCT Pub. Date: Mar. 6, 2008

(65) Prior Publication Data
US 2009/0319010 A1    Dec. 24, 2009

(51) Int. Cl.
*A61F 2/00* (2006.01)
*A61N 1/00* (2006.01)
(52) U.S. Cl. .............................. 607/103; 600/13; 600/14
(58) Field of Classification Search .................. 607/103; 600/411–412, 13–14
See application file for complete search history.

(56) References Cited

FOREIGN PATENT DOCUMENTS

| JP | 55-160720 | | 12/1980 |
|---|---|---|---|
| JP | 61-154575 | | 7/1986 |
| JP | 64-34054 | U | 3/1989 |
| JP | 05-33165 | Y | 8/1993 |
| JP | 05-244607 | | 9/1993 |
| JP | 08-009398 | | 1/1996 |
| JP | 2004167031 | A * | 6/2004 |
| JP | 2004-237050 | | 8/2004 |
| JP | 2004228289 | A * | 8/2004 |
| WO | 2005/117455 | | 12/2005 |

OTHER PUBLICATIONS

Japanese Office Action issued for counterpart Japanese patent application No. 2006-096064 dated Jun. 2, 2011, with English translation.
International Preliminary Report on Patentability issued on counterpart International Patent Application No. PCT/JP2006/316893 dated Mar. 4, 2008.

* cited by examiner

*Primary Examiner* — Linda Dvorak
*Assistant Examiner* — Adam Avigan
(74) *Attorney, Agent, or Firm* — Kratz, Quintos & Hanson, LLP

(57) ABSTRACT

To realize a body surrounding solenoid-type body heating device with small coil impedance which can generate a magnetic flux of predetermined density to one part of the living body near the affected area in the solenoid coil, a body heating device 10 includes a cylindrical solenoid coil 17 in which the body can be inserted easily, a high-frequency power supply 11 to drive the solenoid coil, and a body holder 15 which can be inserted easily in the solenoid coil 17. In the body heating device 10, an across-body direction cross section of the solenoid coil 17 has an arched-shape over a half of the solenoid coil 17 in the peripheral direction and a straight-lined shape in the rest, and a secondary solenoid coil 21 with shorter length and coiled more densely than the solenoid coil 17 is inserted in the solenoid coil 17. A magnetic core 40 which can be inserted easily in the solenoid coil 17 is installed on the body holder 15.

24 Claims, 12 Drawing Sheets

(a)

(b)

(c)

BODY HEATING DEVICE

TECHNICAL FIELD

The present invention relates to a body heating device suitable for partial heating of a living body subject to cancer treatment, and particularly relates to a body heating device for heating the affected area in a body by generating a magnetic flux with a solenoid coil and irradiating the magnetic flux to the body.

The use of the body heating device is suitable for partial thermotherapy (hyperthermia) heating the affected area intensively in order to eliminate cancer cells selectively. It is preferable to inject magnetic-sensitive heat-generating material of fine particles in the body and then apply the alternating magnetic field and heat to the affected area from outside.

BACKGROUND ART

As a body heating device which can heat an inner area of the body intensively in order to treat cancer, a device is known (refer to Patent literature 1) whose magnetic-sensitive heat-generating material mainly includes fine particles of iron oxide restricting relative magnetic permeability to a high rank arranged in the body, and a magnetic flux that passes through the body is formed in the alternating magnetic field generator. As an example of an alternating magnetic field generator, there is a device that irradiates the magnetic flux of along-bodyheight direction, by driving the solenoid coil surrounding the body with an alternating current, and a device that generates a magnetic flux of across-body direction by a pair of magnetic poles which can be arranged at both sides of the body.

Also, in order to ease or prevent dielectrical heating of a surface layer of the body with the high-frequency electric field, a magnetic flux irradiator is known (refer to Patent literature 2) that has a cylinder of high dielectric material in the solenoid coil, the living body can be inserted easily therein. The magnetic flux irradiator is constituted so as to generate a magnetic flux of along-bodyheight direction by driving the solenoid coil with high-frequency current, then irradiate it to almost the whole body laid in the hollow part of the cylinder of high dielectric material. The shape of across-body direction cross section of the solenoid coil, i.e. the cross section of the solenoid radial direction (a cross section perpendicular to the solenoid axial direction), is plane circle.

In addition, there is a magnetic flux irradiator (refer to Patent literatures 3, 4) single-magnetic-pole-working type made so as to irradiate a magnetic flux of high density from one end (the working end) of the magnetic flux generating section to a limited area of the body. These magnetic flux irradiators are constituted of the small solenoid coil with a bar-segment-shaped magnetic core inserted for strengthening the magnetic flux and extending the reach thereof in the solenoid axial direction, and the solenoid coil generates the magnetic flux by high-frequency driving. Also, a device (refer to Patent literature 3) with a flux controlling coil outside the solenoid coil and a short section at the working end for further extending of the reach of the magnetic flux in the solenoid axial direction, and a device (refer to Patent literature 4) arranging the magnetic core thicker-diametered at the non-working end than at the working end, or forming a coolant flow path in the magnetic core for preventing overheat of the magnetic core, are known.

Patent literature 1: Japanese Patent Application Laid-Open No. 11-57031
Patent literature 2: Japanese Patent Application Laid-Open No. 2004-167031
Patent literature 3: Japanese Patent Application Laid-Open No. 2003-205040
Patent literature 4: Japanese Patent Application Laid-Open No. 2004-228289

DISCLOSURE OF THE INVENTION

Problem to be Solved by the Invention

In such conventional body heating devices, the solenoid coil, the living body can be inserted easily therein held on a movable bed, has a cylindrical shape, i.e. the across-body direction cross-sectional shape is plain circle, without any peculiar consideration. In the case that the patient lies on the body holder, the body is substantially located at the center of the circle cross-sectional shape of the solenoid coil.

On the other hand, the affected area to be heated is generally located aside from the center of the body. The high-density part of the magnetic flux formed by the solenoid coil is located at an annular region in the coil near the coil-winding, so in the case that the body-surrounding solenoid typed coil has a large coil diameter and a long periphery, the portion of the periphery, that contributes to heating of the affected area, within the whole magnetic flux of the solenoid coil is substantially limited to a short-segment portion near the affected area and, as a result, the residual portions far from the affected area do not serve for heating. Thus, from the point of view of heating, coil impedance of the residual portions only causes load to the high-frequency power supply, becoming useless.

On the other hand, the portions far from the affected area also must be preserved to flow the electric current, thus the residual portions cannot be excluded from the solenoid coil.

However, in the case that the coil impedance is large, high voltage must be applied to the solenoid coil to secure required coil current; accordingly, a high-frequency power supply with large output is necessary and costs increase. In addition, high-quality materials are required for insulation measures to secure safety, and costs further increase.

Thus, a first technical subject is to realize a solenoid type heating device with small coil impedance but can generate a magnetic flux of predetermined density at the portion near the affected area within the solenoid coil.

In addition, even if most of the affected area to be heated is aside from the body center, their position is not decisively near the solenoid coil-winding, and so it is important to extend the reach of the magnetic flux in the solenoid radial direction. The reach of the magnetic flux in the solenoid axial direction can be extended by inserting a magnetic core comprising ferromagnetic materials such as ferrite in the solenoid coil; however, in order to extend the reach of the magnetic flux in the solenoid radial direction, it is necessary to increase coil current without changing the specification of the solenoid coil shape.

However, in the case that coil current increases, the voltage applied to the solenoid also rises generally, and as mentioned above, the scale of the power supply and the burden for securing safety are big. On the other hand, even if a solenoid-type body-surrounding heating device is used, the affected area do not range the overall length of the solenoid coil, thus only in a part of the solenoid axial direction, extension of the magnetic flux reach in the solenoid radial direction is required.

Here, a second technical subject is to realize a body-surrounding solenoid-type body heating device which can cause a desired density of the magnetic flux in parts far from the coil-winding and near the center of the solenoid coil.

In the conventional devices of various types to heat a living body, described above, the body-surrounding solenoid type that irradiates the magnetic flux running on the whole body delivers the magnetic flux to deep area inside the body; the magnetic flux includes a group of almost parallel magnetic force lines, so the decreasing gradient of the magnetic flux density in the direction along the magnetic flux is small, ranging over almost the whole body, thus the generation of undesired hot spots is little. However, the problem is that it is difficult to concentrate the magnetic flux on a desired part such as magnetic-sensitive heat-generating material arranged at the affected area.

For this, in a single-magnetic-pole-working type generating a partial magnetic flux, the magnetic flux concentrates near the working end, and an area near the body surface can be heated sufficiently. However, because the magnetic flux spreads as it gets far from the working end, thus, the decreasing gradient of the magnetic flux density in the direction along the magnetic flux is steep, but thereupon, if the coil current is increased to heat a deeper area, the magnetic flux density of the body surface becomes excessive. As a result, the normal cells of the body surface are also heated undesirably with inductive current.

In a type of magnetic pole-pair that generating an across-body direction magnetic flux, a characteristic between said body-surrounding type and said single-magnetic-pole type appears, and the spreading of the magnetic flux and the decreasing gradient of the magnetic flux density also becomes medium. As a result, both advantages and disadvantages become balanced in this type.

However, to increase the effect of partial thermotherapy by using a body heating device, it is required to reinforce the characteristic in which the magnetic flux reaches an affected deeper area of the body densely, in addition, keeping low the magnetic flux density on normal body surface.

Thus, a third technical subject is to realize a body heating device whose concentration and spreading of the magnetic flux can be carried out freely and clearly even in inner areas of the body. And a fourth technical subject is to create the device of thus reinforced magnetic flux characteristic with a form able to use easily.

Means for Solving the Problems

The body heating device according to the present invention (claim 1) is created to solve the first to the fourth technical subjects, in the body heating device comprising:

a cylindrical solenoid coil in which the living body can be inserted easily;

a high-frequency power supply to drive the solenoid coil; and a body holder such as a movable bed which can be inserted easily in the solenoid coil, wherein an across-body direction cross section of the solenoid coil has arched-shape over a half of the solenoid coil in the peripheral direction, and a straight-line shape in the rest of the solenoid coil (hereinafter, said cross-sectional shape is referred to as "D-shaped"), and a secondary solenoid coil with shorter length and coiled more densely compared with the solenoid coil is inserted in the solenoid coil. In the secondary coil, the driving power is fed from the above-mentioned, or other high-frequency power supply. Further, a magnetic core which can be inserted easily in the solenoid coil is provided on the body holder.

"Arched shape" used here typically indicates a segment of an almost perfect circular shape, and also includes oval/parabolic/hyperbolic segments. In other words, it indicates "the second order curve profile" or "conic section profile".

"Straight-line shape" includes a shape having a gentle flexure or curve not similar to a coil curve that contributes to increase inductance and is not restricted to a "completely straight shape". For example, a shape with flexure generated as reaction in forming "arched shape" in the case that making a D-shaped coil is also included.

A preferable range of "straight-line shape" is different according to the shape of a part having "arched shape" In the case in which the ratio of the "average radius of curvature on a straight-line part: to the average radius of curvature on an arched part" is equal to or more than "10:1" in both shapes, the effect of the invention can be considered successful enough.

The body heating device according to the present invention (claim 2) is the body heating device according to claim 1, wherein a cross-sectional area of the magnetic core decreases toward the top, which is used as a working end.

Further, the body heating device according to the present invention (claim 3) is the body heating device according to claim 2, wherein a body surface temperature detector for detecting a temperature on a body surface facing to the working end is installed on the working end of the magnetic core.

The body heating device according to the present invention (claim 4) is the invention extracting a requirement to solve the first technical subject among aforementioned technical subjects. Concretely, the invention is a body heating device comprising a cylindrical solenoid coil with a shape enough to insert the body easily, a high-frequency power supply for driving the coil and a body holder such as a movable bed which can be inserted easily in the solenoid coil, wherein an across-body direction cross section of a solenoid coil has an arched-shape over a half of the solenoid coil in the peripheral direction, and has a straight-line shape in the rest of the solenoid coil, in order to solve the first technical subject.

The body heating device according to the present invention (claim 5) is directed to solve the second technical subject as well as the first technical subject, and it is the body heating device according to claim 4, wherein a secondary solenoid coil having shorter length and coiled more densely compared with the solenoid coil is inserted in the solenoid coil. In the secondary solenoid coil, power is fed from the above-mentioned or other high-frequency power supply.

The body heating device according to the present invention (claim 6) is directed to solve the second technical subject in a high level as well as the first technical subjects, and it is the body heating device according to claim 5 wherein a coiling density of the secondary solenoid coil is dense near an arched part of the solenoid coil and sparse at near the straight-line part of the solenoid coil.

More concretely, if the body holder is biased near the straight part of the solenoid coil, the coiling density of the solenoid coil is dense at the anti-biased side and sparse at the biased side of the body holder. If the holder is biased near the arched part of the solenoid coil, the coiling density of the secondary solenoid coil is dense at the biased side and sparse at the anti-biased side of the body holder.

In addition, the body heating device according to the present invention (claims 7, 8) is the body heating device according to claim 6 or 5 wherein the secondary solenoid coil can be inserted in or extracted from the solenoid coil freely.

The body heating device according to the present invention (claim 9) is directed to solve the third technical subject as well as the first technical subject, and it is the body heating device according to claim 4 wherein a magnetic core which can be inserted easily in the solenoid coil is arranged.

The body heating device according to the present invention (claim 10) is directed to solve the third technical subject as well as the first and second technical subjects, and it is the body heating device according to claim 5, wherein the magnetic core which can be inserted easily in the solenoid coil is arranged.

The body heating device according to the present invention (claim 11) is the invention to solve the second technical subject among the aforementioned technical subjects. Concretely, is a body heating device comprising: a cylindrical solenoid coil with a shape enough to insert the body easily; a high-frequency power supply to drive the solenoid coil; and a body holder such as a movable bed which can be inserted easily in the solenoid coil, wherein a secondary solenoid coil having shorter length and coiled more densely compared with the solenoid coil is inserted in the solenoid coil, to solve the second technical subject. In the secondary coil, power is fed from the above-mentioned, or other high-frequency power supply.

The body heating device according to the present invention (claim 12) is directed to solve the third technical subject as well as the second technical subject, and it is the body heating device according to claim 11 wherein a magnetic core which can be inserted easily in the solenoid coil is arranged.

The body heating device according to the present invention (claim 13) is the invention to solve the third technical subject among the aforementioned technical subjects. Concretely, the invention is a body heating device comprising a cylindrical solenoid coil with a shape enough to insert the body easily, a high-frequency power supply for driving the coil and a body holder such as a movable bed which can be inserted easily in the solenoid coil, wherein a magnetic core which can be inserted easily in the solenoid coil is provided to solve the third technical subject.

In addition, the body heating device according to the present invention (claim 14) is directed to solve the third technical subject in a high level, and it is the body heating device according to any one of claims 9, 10, 12 and 13, wherein a plural magnetic core is provided being separately located in the axial direction of the solenoid coil.

In addition, the body heating device according to the present invention (claim 15) is the body heating device according to claim 14 wherein a plural magnetic core includes a solid magnetic core for converging the magnetic flux, and a hollow magnetic core for dispersing the magnetic flux.

In addition, the body heating device according to the present invention (claim 16) is the body heating device according to claim 15, wherein a cross-sectional area of the solid magnetic core decreases toward the top, which is used as a working end.

The body heating device according to the present invention (claim 17) is the body heating device according to claim 15 wherein the solid magnetic core is installed on the body holder.

The body heating device according to the present invention (claim 18) is the body heating device according to claim 15 wherein a body surface temperature detector for detecting a temperature on a body surface facing to the working end is installed on the working end of the solid magnetic core.

The body heating device according to the present invention (claim 19) is the body heating device according to claim 15 wherein an inner temperature of the solid magnetic core detector for detecting an inner temperature is installed in the solid magnetic core.

The body heating device according to the present invention (claim 20) is the body heating device according to claim 15 wherein the hollow magnetic core is a complex of a ferromagnetic material and a polymerized material (polymer).

The body heating device according to the present invention (claim 21) is the body heating device according to claim 15 wherein a small solenoid coil driven by the above-mentioned or other high-frequency power supply is coiled on the solid magnetic core.

The body heating device according to the present invention (claim 22) is the body heating device according to claim 21 wherein a magnetic core cooling means for cooling the solid magnetic core is further provided.

Effect of the Invention

In such the body heating device according to the present invention (claims 1, 4, 11, 13), the advantage is that the body can be easily inserted in the solenoid coil together with the body holder; it has also a device of an along-bodyheight direction magnetic flux irradiation type, i.e. a body-surrounding solenoid type in which the magnetic flux disperses over the entire body, securing that it reaches deep areas of the body.

Further, by changing the shape of the solenoid coil with an across-body direction from plain circle shaped to a cross-sectional D-shaped (claims 1, 4), the magnetic flux density generated in the affected area does not decrease because the coil shape of the portion contributing to form the magnetic field near by the affected area remains an arched shape. On the other hand, the coil shape of the portion which cannot contribute to form the magnetic flux near by the affected area is formed into a straight-line shape, thus, depending on the shape, both the self inductance of the coiled conductor and the mutual inductance between coiled conductors are low. In addition, the coiled path shortens inwardly, reducing inductance in both shape factor and length factor, and reducing resistance in the length factor, resulting in impedance reduction.

Thus, according to the present invention (claims 1, 4), a body heating device of the body-surrounding solenoid type, a magnetic flux of expected density can be generated near by the affected area in the solenoid coil thereby, and has small coil impedance is realized, solving the first technical subject.

In the body heating device according to the present invention (claim 1, 11, 5), by introducing a secondary solenoid coil more densely wound and shorter than the solenoid coil into the solenoid coil, while maintaining the advantage of the body-surrounding solenoid type in which the magnetic flux disperses over the entire body and reaches deep areas, in the case that the secondary solenoid coil is driven with the same phase as the solenoid coil is in a series connection with the solenoid coil, for example, the produced ampere turn, i.e. the product of coil current and coiling number, increases at the secondary solenoid coil arrangement part in the solenoid axial direction, the magnetic field is reinforced and the reach of the magnetic flux in the solenoid radial direction extends. Therefore, in the case that the affected area is placed in the secondary solenoid coil, a magnetic flux of expected density is irradiated even if the affected area is at a side of the center apart from the solenoid coil winding viewed in the solenoid radial direction.

Thus, with this invention, a body heating device of body-surrounding solenoid type which can generate, regarding in partial zone of the solenoid axial direction, a magnetic flux with expected density to a near centered part apart from the solenoid coil winding is realized, and the second technical subject can be solved.

In this case, although the burden such as power supply scale increases owing to the magnetic flux reinforcement, it is a useful burden that contributes to heat the affected area, which is different from the aforementioned useless burden related to a portion in a peripheral direction far from the affected area in the solenoid coil.

In the body heating device according to the present invention (claim 1, 13, further claims 9, 10 and 12), by easily inserting a magnetic core in the solenoid coil, the magnetic flux converges in the magnetic core and its density increases, while maintaining the advantage of the body-surrounding solenoid type in which the magnetic flux disperses over the entire living body and reaches deep areas of the body; therefore, by pointing the magnetic core at the affected area, the magnetic flux can reach deeper areas in the living body while maintaining high density, and can disperse at the areas other than the affected area.

In other words, in the hollow part of the solenoid coil, almost all the magnetic flux extends over the solenoid coil in an axial direction, then while maintaining the state in the axial direction, converges in a radial direction at the magnetic core, and disperses at the other position. And, the magnetic flux, converged in the magnetic core, does not spread immediately and disperses largely as soon as it emerges from the magnetic core, but advances in the axial direction of the solenoid coil while further dispersion is restricted in the hollow part of the solenoid coil. Thus, the magnetic flux is still maintained in a high density state at the neighborhood of the magnetic core, and then gradually dispersed.

Thereby, the characteristic of dispersion of the magnetic flux is stronger than the type for generating an across-body direction magnetic flux and similar to the type generating the along-bodyheight direction magnetic flux. The characteristic of the magnetic flux concentration is stronger than the type for generating an across-body direction magnetic flux and similar to the type for generating a limited-area-pointed magnetic flux. Further, the reach of a magnetic flux with high density increases compared with conventional devices.

Thus, according to the present invention, the third technical subject can be solved by realizing a body heating device capable of converging and dispersing the magnetic flux freely and clearly even in inner area of the body.

In the body heating device according to the present invention (claims 1, 17), a magnetic core for reinforcing the magnetic flux is mounted on the body holder, then the magnetic core is inserted in the solenoid coil linked with the insertion of the body holder, facilitating the device use, thus solving the fourth technical subject.

In the body heating device according to the present invention (claims 2, 16), the magnetic core for reinforcing the magnetic flux is narrowed toward the working end, then the degree of concentration of the magnetic flux is improved, and the third technical subject can be solved in a high level.

In addition, in the body heating device according to the present invention (claims 3, 18), the temperature of the affected area near or on the body surface can be easily detected by a body surface temperature detector directing the working end of the magnetic core to the affected area of the body.

In this way, undesired heating of the body can be prevented by controlling the output of the high-frequency power supply based on the detected temperature.

Thus, according to the present invention, the body heating device, concentration and dispersion of the magnetic flux can be carried out freely and clearly thereby even in deep areas inside the body, besides, can be used safely even with its high magnetic flux concentration capability, is realized.

In the body heating device according to the present invention (claim 6), as for the device whose body holder is at a side of the straight-line part of the solenoid coil, in the case that the body of the patient is laid along the body holder before using the device, by the arrangement that the affected area and the body holder are biased in the opposite side in respect of solenoid coil center from each other viewed in solenoid radial direction, the affected area is directed to the arched side of the coil. On the other hand, as for the device whose body holder is on the arched part of the solenoid coil, in the case that the body of the patient is laid on the body holder before using the device, by the arrangement that the affected area and the body holder are biased in the same side in respect of solenoid coil center viewed in the solenoid radial direction, the affected area is also directed to the arched side of the coil. Therefore, in any case, the state that the affected area is located in the vicinity of the arched part of the solenoid coil can be arranged.

Further, while maintaining said state, the coiling density of the secondary solenoid coil is dense at the arched-shaped side, i.e. in the vicinity of the affected area, and sparse at parts other than the affected area, so the magnetic flux concentrates on the affected area side and disperses on other parts.

Thus, according to the present invention, even if the affected area is at a side of the solenoid coil center apart from the solenoid coil winding, a body heating device of a body-surrounding solenoid type which can concentrate the magnetic flux at such area with an expected density can be realized, and the second technical subject can be solved in a high level.

In the body heating device according to the present invention (claims 7, 8), the secondary solenoid coil can be inserted in or extracted from the solenoid coil freely, and therefore appropriate irradiation of the magnetic flux on the affected area can be carried out such that the reinforcing of the magnetic flux in the secondary solenoid coil can be selectively adopted by the part for reinforcing the magnetic flux in the secondary solenoid coil can be changed, and the magnetic flux reinforcing part can be limited to a narrow range by using the secondary solenoid coil as small-diametered as the part of the living body which has the affected area can be inserted therein.

In the body heating device according to the present invention (claim 14), a plural magnetic core is mounted separately in the axial direction of the solenoid coil, reinforcing concentration of the magnetic flux from both sides of the magnetic cores, and accordingly a high-density part of the magnetic flux extends in the axial direction. In this way, the magnetic flux with high density can be irradiated to areas of the body deeper than conventional manner.

Thus, according to the present invention, body heating device concentration and dispersion of the magnetic flux can be carried out freely and clearly even to deep areas inside the body, solving the third technical subject in a high level.

In the body heating device according to the present invention (claim 15), together with a solid magnetic core for converging the magnetic flux, a hollow magnetic core for dispersing it is easily inserted in the solenoid coil and mounted separately in the axial direction, thereby improving both dispersion ability and convergence capability of the magnetic flux.

Thus, according to the present invention, concentration and dispersion of the magnetic flux can be carried out freely and clearly even to deep areas of the body, solving the third technical subject in a high level.

In the body heating device according to the present invention (claim 19), the inner temperature of the solid magnetic core, the temperature of which tends to increase depending on the magnetic flux convergence capability of high level, can be detected by the inner temperature detector.

Therefore, by controlling the output of the high-frequency power supply based on the detected temperature, undesired temperature increase of the magnetic core can be prevented. The magnetic core has a property to vary the magnetic flux depending on the temperature; concretely, the magnetic flux convergence capability decreases as the temperature increases, so to ensure treatment effect, it is effective to keep the temperature of the solid magnetic core near normal temperature with its working end directed to the affected area of the body at the time of use. For example, in the case that the small solenoid coil is coiled on the solid magnetic core and temperature increases in high level, it is preferable to cool the solid magnetic core depending on the detected temperature.

BRIEF DESCRIPTION OF THE DRAWINGS

FIG. 1(c) is an along-bodyheight direction cross-sectional view of a magnetic flux irradiator (sectioned along the solenoid axial direction).

FIG. 2(a) is an across-body direction cross-sectional view (sectioned along the solenoid diameter direction) of the body heating device and FIG. 2(b) is a perspective view of a magnetic core.

FIG. 3(a) is a plane-viewed along-bodyheight direction cross-sectional schematic view (sectioned along the solenoid axial direction) and FIG. 3(b) is a side-viewed along-bodyheight direction cross-sectional schematic view (sectioned along the solenoid axial direction).

FIG. 4(a) is a perspective view of the body heating device, FIG. 4(b) is a along-bodyheight direction cross-sectional view of the magnetic flux irradiator (sectioned along the solenoid axial direction), FIG. 4(c) is an across-body direction cross-sectional view (sectioned along the solenoid diameter direction) of the magnetic flux irradiator, and FIG. 4(d) is a side-viewed along-bodyheight direction cross-sectional schematic view (sectioned along the solenoid axial direction) of the magnetic flux irradiator.

FIG. 5(a) is a perspective view of the body heating device, FIG. 5(b) is an along-bodyheight direction cross-sectional view of the magnetic flux irradiator, FIG. 5(c) is an across-body direction cross-sectional view of the magnetic flux irradiator, and FIG. 5(d) is a side viewed along-bodyheight direction cross-sectional schematic view of the magnetic flux irradiator.

FIG. 6(a) is a side-viewed along-bodyheight direction cross-sectional view of a solenoid coil and a body holder and FIG. 6(b) is a side-viewed along-bodyheight direction cross-sectional schematic view of the device in the case that the magnetic flux is irradiated.

FIG. 7(a) is a side-viewed along-bodyheight direction cross-sectional view of the solenoid coil and the body holder and FIG. 7(b) is a side-viewed along-bodyheight direction cross-sectional schematic view of the device in the case that the magnetic flux is irradiated.

FIG. 8(a) is a perspective view of the body heating device, FIG. 8(b) is a side-viewed along-bodyheight direction cross-sectional view of the magnetic flux irradiator, and FIG. 8(c) is a side-viewed along-bodyheight direction cross-sectional schematic view of the device in the case that the magnetic flux is irradiated.

FIG. 9(a) is a perspective view of the body heating device, FIG. 9(b) is a side-viewed along-bodyheight direction cross-sectional view of the magnetic flux irradiator, and FIG. 9(c) is a side-viewed along-bodyheight direction cross-sectional schematic view of the device in the case that the magnetic flux is irradiated.

FIG. 10(a) is a perspective view of the body heating device, FIG. 10(b) is a side-viewed along-bodyheight direction cross-sectional view of the magnetic flux irradiator, and FIG. 10(c) is a side-viewed along-bodyheight direction cross-sectional schematic view of the device in the case that the magnetic flux is irradiated.

FIG. 11(a) is a perspective view of the body heating device, FIG. 11(b) is a side-viewed along-bodyheight direction cross-sectional view of the magnetic flux irradiator, and FIG. 11(c) is a side-viewed along-bodyheight direction cross-sectional schematic view of the device in the case that the magnetic flux is irradiated.

FIG. 12(a) is a perspective view of the body heating device, FIG. 12(b) is a side-viewed along-bodyheight direction cross-sectional view of the magnetic flux irradiator, FIG. 12(c) is a perspective view of a solid magnetic core, and FIG. 12(d) is a perspective view of a hollow magnetic core.

DESCRIPTION OF THE REFERENCE NUMERALS

Figure 1:
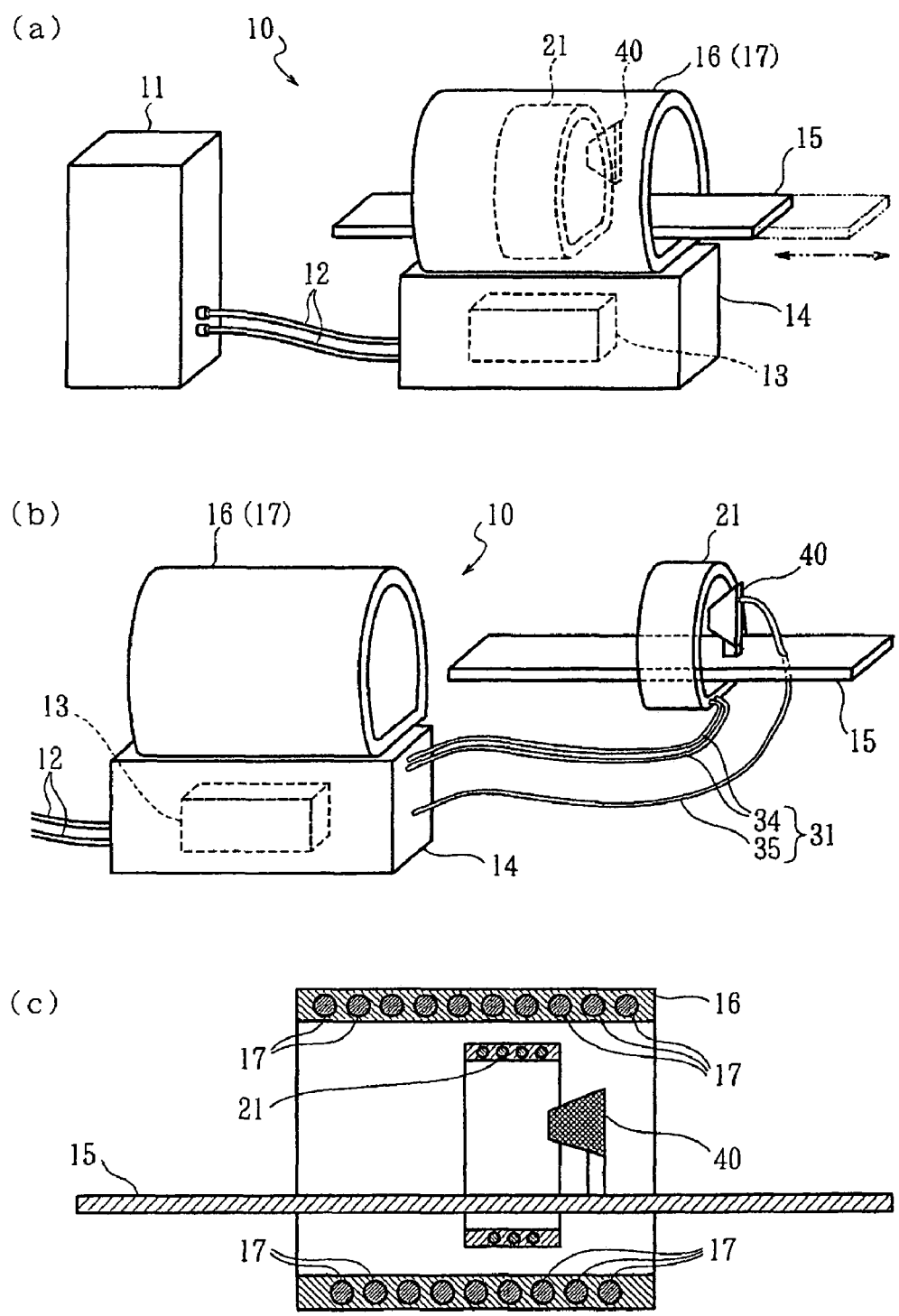
FIG. 1 illustrates a structure of a body heating device of one embodiment according to the present invention (a first embodiment), where FIGS. 1(a) and (b) are perspective views of the body heating device.

8 . . . patient (body subject to be irradiated), 8a . . . affected area, 9 . . . magnetic flux
10 . . . body heating device
11 . . . high-frequency power supply, 12 . . . cable,
13 . . . matching box, 14 ... mount, 15 ... movable bed (body holder), 16 ... hollow frame,
17 ... solenoid coil, 17a ... arched shape part, 17b ... straight-line part,
18 ... hollow frame, 19 ... solenoid coil,
21, 22 ... secondary solenoid coil, 22a ... densely coiled part, 22b ... sparsely coiled part,
23, 24 ... secondary solenoid coil, 28 ... small solenoid coil,
31 ... cable, 34 ... high-frequency power line,
35, 36 ... signal line,
37 ... piping, 38 ... cooling water circulator,
40 ... solid magnetic core, 41 ... core-body, 42 ... working end,
43 ... non-working end, 47 ... coolant path,
48, 49a, 49b ... magnetic core,
50 ... hollow magnetic core, 51 ... core-body,
52 ... hollow frame,
61 ... body surface temperature detector,
62 ... inner temperature detector,
110, 120, 130, 140, 150 ... body heating device,
160, 170, 180, 190 ... body heating device

BEST MODE FOR CARRYING OUT THE INVENTION

Regarding a body heating device of one embodiment according to the present invention (a first embodiment), the structure will be described referring to the attached drawings. FIGS. 1(a), 1(b) are a perspective view of the body heating device 10, FIG. 1(c) is an along-bodyheight direction sectional view of a magnetic flux irradiator (a cross section in the solenoid axial direction), FIG. 2(a) is an across-body direction cross-sectional view of the magnetic irradiation part (a cross section in the solenoid diameter direction), and FIG. 2(b) is a perspective view of a solid magnetic core 40.

Regarding drawings of the rest of the embodiments, only elements required to describe the present invention or related to the invention are illustrated and excessively detailed illustrations are omitted for description simplification.

Regarding the magnetic flux irradiator structure, an along-bodyheight direction sectional view illustrates a cross-sectional view including the horizontal solenoid axis, in a state in which a body surrounding type solenoid, i.e. the main part of the magnetic flux irradiator, is put as the axis thereof is direction horizontal, and an across-body direction cross-sectional view illustrates a cross-sectional view in the solenoid diameter direction, i.e. a vertical plane perpendicular to the horizontal solenoid axis in the above-mentioned state.

A body heating device 10 (refer to FIG. 1(a) to (c)) is suitable for partial thermotherapy such as in bladder cancer and cauda equina neuroma, and as a conventional device of the body surrounding solenoid type, the body heating device 10 includes a movable bed 15 (body holder) with a horizontally-feeding mechanism not shown, a hollow frame 16 laid on a mount 14, a large solenoid coil 17 stored in a hollow frame 16 whose axial direction is set horizontally and in which the movable bed 15 can be inserted easily, and a high-frequency power supply 11 for feeding high-frequency current to the solenoid coil 17 through a cable 12 and a matching box 13. However, the three following points are different from the conventional device, i.e. main differences between the body heating device 10 and the conventional device of the body surrounding solenoid type: an across-body direction cross-sectional shape of the solenoid coil 17 and the hollow frame 16 is D-shaped, a secondary solenoid coil 21 is inserted in the solenoid coil 17, and a solid magnetic core 40 mounted on the movable bed 15 is inserted in the solenoid coil 17.

These differences are described in detail as follows. The first difference between the present invention and a conventional device, i.e. the solenoid coil 17 with an across-body direction cross-sectional D-shaped, will be described. In the case that the patient is laid on the movable bed 15, the movable bed 15 is placed in a biased position lower than the solenoid axis in the hollow part of the solenoid coil 17 so that the patient is in a center of the solenoid coil 17, however, said biased side of the solenoid is changed in shape. The across-body direction cross-sectional shape of the solenoid coil 17 is substantially uniform throughout the entire length of the solenoid coil 17, and the across-body direction cross-sectional shape will be described in detail as follows, (refer to FIG. 2(a)). In the solenoid coil 17, the part thereof, extending from the both wing areas to the upper area, of the movable bed, i.e. the anti-biased side (contrary of said biased side) has arched shapes like the conventional device, and the arched part 17a occupies a half or more of an imaginary circle in the extension. However, in the solenoid coil 17, a lower part of the solenoid coil 17 which is the biased side regarding the movable bed 15 is constituted as a straight-line part 17b.

The straight-line part 17b forms a straight-line except the transition part at both ends thereof, and extends through the inside of the conventionally existing virtual circle, thus, connecting both ends of the upper arched parts by a short linear course. An example is given that shows the width of the straight-line part 17b and of the movable bed 15 is almost the same, but depending on the relation with other members, a difference between both widths may occur. Also, the straight-line part 17b may differ from a perfect straight-line and be approximately straight. For example, the straight-line part 17b may be a line slightly bent or curved with a large radius of curvature, thus, in case that its shape is closer to a straight-line than the shape of the arched part 17a, it can be considered as a straight-line shape.

As the second difference between the present invention and the conventional device, the structure of the secondary solenoid coil 21, will be described (refer to FIG. 1, FIG. 2(a)). The secondary solenoid coil 21 is formed same as the solenoid coil 17, such that the movable bed 15 arranged horizontally also can be easily inserted therein, besides the coil 21 has a D-shaped smaller than the solenoid coil 17 in the across-body directional cross-section so as to be inserted in the solenoid coil 17. Thus, in an across-body direction cross-sectional shape thereof, the non-biased side regarding the movable bed 15 has an arched-shape, on the other hand, the biased side regarding the movable bed 15 has a straight-line shape. In addition, the coil 21 is shorter than the solenoid coil 17, and has a coiling density, denser than the solenoid coil 17, with smaller coiling pitch, using smaller-diametered conductor material than the solenoid coil 17.

As numerical value examples comparing both coils, in the solenoid coil 17 the diameter of the arched part 17a is about 500 mm, the wire diameter is about 20 mm, the coiling pitch is about 50 mm, and the number of coiling turn is about 10 turns.

On the other hand, in the secondary solenoid coil 21 the diameter of the arched part is about 470 mm, the wire diameter is about 10 mm, the coiling pitch is about 20 mm, and the number of coiling turn is about 4 turns.

This secondary solenoid coil 21 is inserted in the solenoid coil 17 and located at the center in the solenoid axial direction or its vicinity, in a way being moved in an axial direction solely or together with the movable bed 15. To drive the coil 21 simply and securely in the same phase, the coil 21 is connected in series with the solenoid coil 17 using the high-frequency electric wire 34 in a flexible cable 31.

In relation to the third difference between the present invention and the conventional device, the structure of the solid magnetic core 40, will be described (refer to FIG. 1, FIG. 2(*a*)). The solid magnetic core 40 has ferromagnetism flux with high magnetic permeability to irradiate the affected area 8*a* as a target, and is installed on the upper side of the movable bed 15, i.e. the face the patient 8 is laid thereon. The magnetic core 40 fixed on the upper part of the movable bed 15 with a simple strut is illustrated. A height adjusting mechanism may be added, or the magnetic core 40 may be inserted in the movable bed 15. The solid magnetic core 40 mainly includes a comparatively small core-body 41 that is put between the thighs, at the root thereof, of the patient to irradiate prostate cancer, for example (refer to FIG. 2(*b*)). The said core-body 41 is made of ferromagnetic materials, and has a pyramidal or cornical shape, with a cross section decreasing toward the top, and with a flattened or curved narrow plane at the top, for example. The core-body 41 is arranged directing the top thereof to the affected area as an working end 42 and is installed on the movable bed 15 directing the axis line thereof in parallel with the bodyheight direction of the movable bed 15 (refer to FIG. 1).

Figure 2:
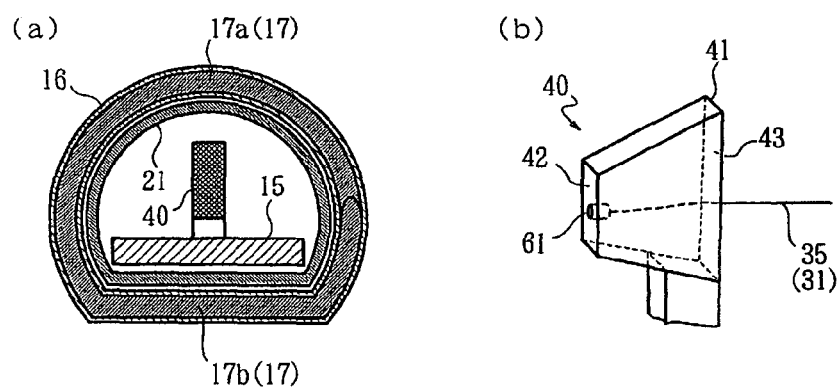
FIG. 2 illustrates a structure of the body heating device, where

The body surface temperature detector 61 is installed on the working end 42 of the core-body 41 to detect temperature of the body surface facing to the working end 42 (refer to FIG. 2). The body surface temperature detector 61 includes a thermometer with a semiconductor sensor, for example. To measure the surface temperature of the affected area, the temperature detector 61 is embedded in the working end 42 except the thermosensitive part, and the parts other than the thermosensitive one are covered with a heat insulator. The body surface temperature detector 61 is connected to the high-frequency power supply 11 in a signal line 35 that protrudes toward a side of a non-working end 43 through the core-body 41, and the temperature detected by the body surface temperature detector 61 can be used for controlling high-frequency driving power. For example, if the temperature detected by the body surface temperature detector 61 exceeds 42° C., output from the high-frequency power supply 11 is decreased. In this connection, the signal line 35 passes through the movable bed 15 and reaches the mount 14 together with the high-frequency power line 34 contained in the cable 31, then reaches the high-frequency power supply 11 contained in the cable 12, for example.

Figure 3:
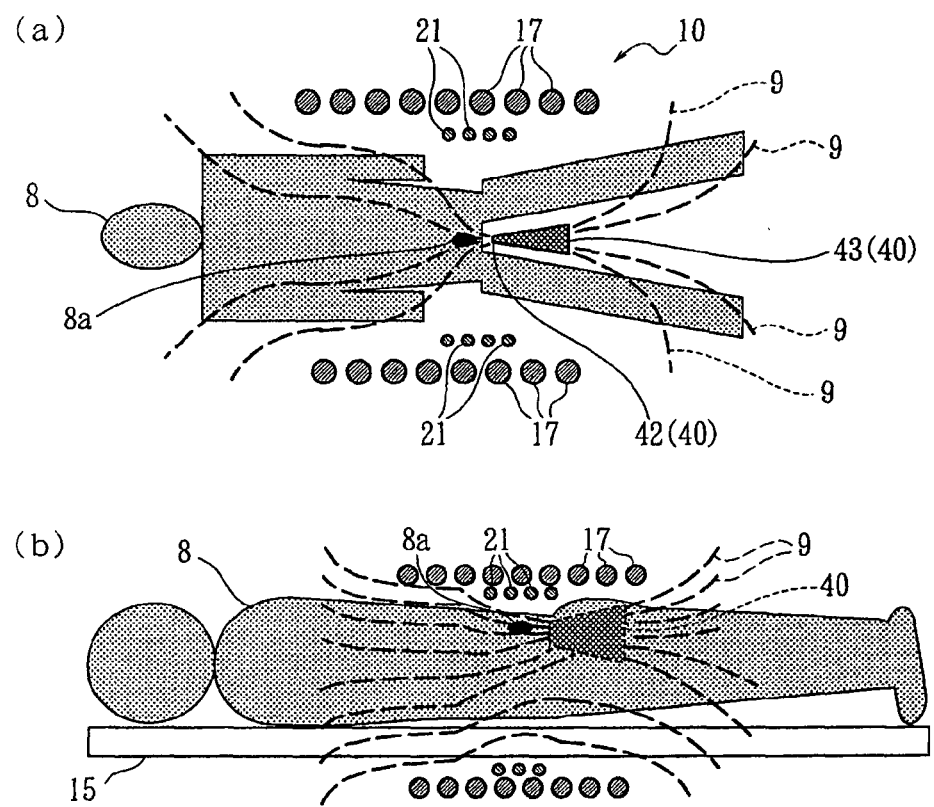
FIG. 3 illustrates a use of the body heating device, where

Regarding the body heating device 10 of the first embodiment, use and operation thereof will be described referring to the attached drawings. FIG. 3 shows in the case that magnetic flux is irradiated to the patient 8 (the body, the body to be irradiated), FIG. 3(*a*) is a plane-viewed along-bodyheight direction cross-sectional schematic view (sectioned along the solenoid axial direction) and FIG. 3(*b*) is a side-viewed along-bodyheight direction cross-sectional schematic view (sectioned along the solenoid axial direction).

The patient 8 in whom fine particles of a magnetic-sensitive heat-generating material are injected is laid on the movable bed 15 so that the affected area 8*a* is directed upward; for example, if the affected area 8*a* is in the lumbar part, the patient is laid on his stomach.

Then, the solid magnetic core 40 is put between the thighs at the root thereof, directing the working end 42 to the abdominal region of the patient 8, and directing the non-working end 43 to the tiptoes of the legs. Next, the secondary solenoid coil 21 is slid in the along-bodyheight direction of the movable bed 15 and placed on a part surrounding the affected area of the patient 8. As a result, a relative position among the solid magnetic core 40, the secondary solenoid coil 21 and the patient 8 is fixed on the basis of the movable bed 15, and maintaining this condition, the movable bed 15 is moved to send the patient 8 into the hollow frame 16 namely into the hollow part of the solenoid coil 17.

Then the high-frequency power supply 11 is operated with a timing that the magnetic-sensitive heat-generating material is deposited on the affected area, thus, a magnetic flux 9 is generated extending in the axial direction of the solenoid coil 17, i.e. the body-height direction of the patient 8. The magnetic flux 9 is focussed entirely and generally by the secondary solenoid coil 21, converged further by the core-body 41 in the solid magnetic core 40, then irradiated densely to the inner area of the body. If the temperature of the affected area of the patient increases undesirably, it is detected by the body surface temperature detector 61, and the output of the high-frequency power supply 11 is suppressed so that the normal body surface of the patient 8 is not heated undesirably even if near the affected area.

Regarding body surface apart from the affected area, the magnetic flux that penetrates it diffuses or disperses, and the gradient of the magnetic flux density is retained small; accordingly the amount of induced current by the alternating magnetic field is small, undesirable heating of the surface is avoided. Thus, in the body heating device 10, the magnetic flux of high density is irradiated on areas affected for example with prostate cancer, i.e. a limited area of the depth of the body is heated sufficiently with no side effects to the patient 8.

Regarding high-frequency feeding to the solenoid coil 17 and the secondary solenoid coil 21, output of the high-frequency power supply 11 is adjusted so that the magnetic flux 9 is dense enough to treat the affected area 8*a*. At this time, an irradiation magnetic flux with the same density of a conventional device can be applied to the affected area with output voltage lower than the conventional device. This is because the impedance of the solenoid coil 17 decreases at the same number of coiling turn as the plain circular coil of the conventional device, owing to the modification of the coil shape to the shape having straight-lined part 17*b*, thereby coil current and magnetic flux density are enlarged than the conventional device with same output voltage.

Figure 4:
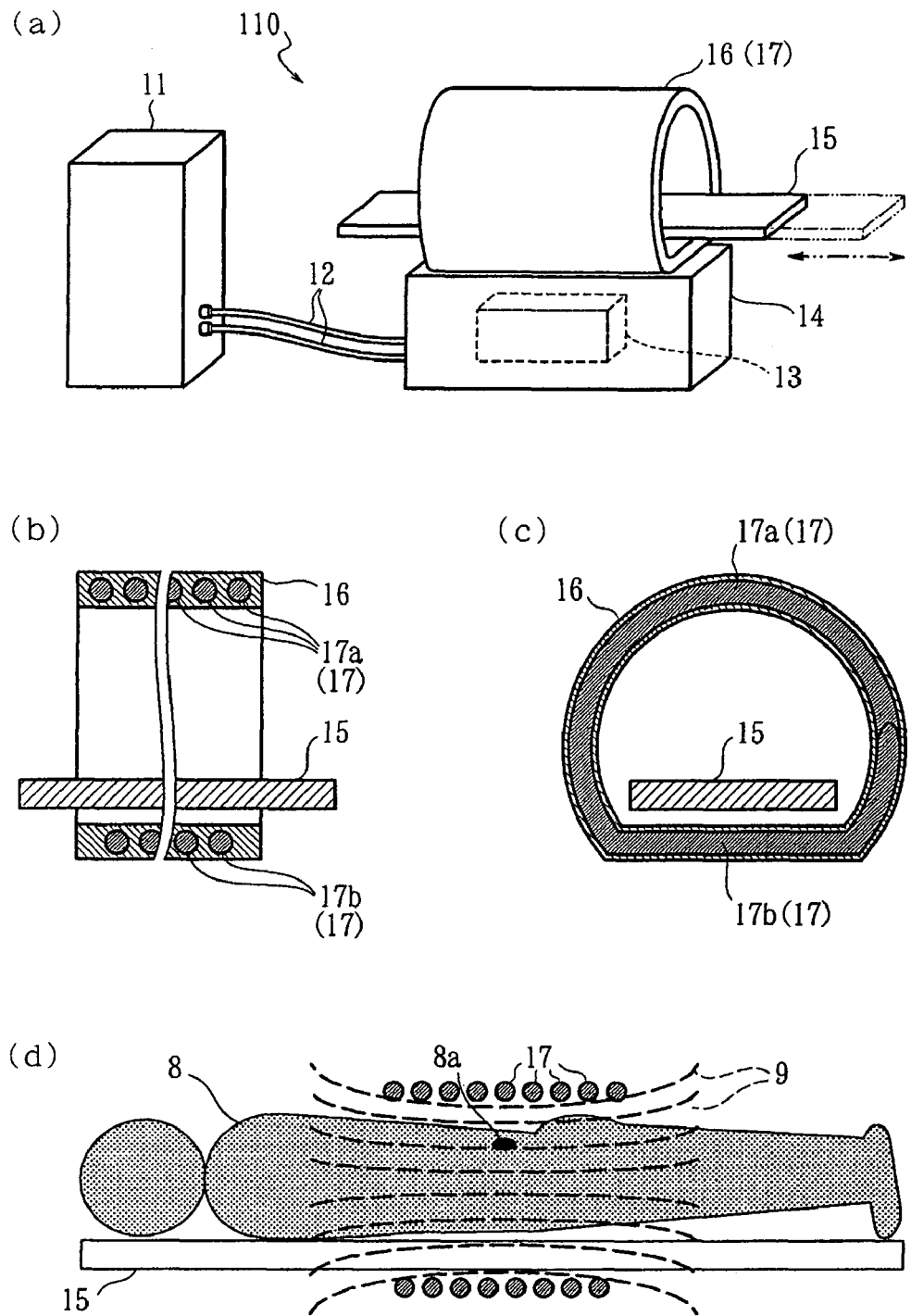
FIG. 4 illustrates a structure and a use of a body heating device of other embodiment according to the present invention (a second embodiment), where

Regarding a second embodiment of the body heating device according to the present invention, the structure thereof will be described referring to the attached drawings. FIG. 4(*a*) is a perspective view of the body heating device, FIG. 4(*b*) is a along-bodyheight direction cross-sectional view of the magnetic flux irradiator (sectioned along the solenoid axial direction), FIG. 4(*c*) is an across-body direction cross-sectional view (sectioned along the solenoid diameter direction) of the magnetic flux irradiator.

The body heating device 110 includes the mount 14, the movable bed 15, the hollow frame 16, the solenoid coil 17 and the high-frequency power supply 11 like the conventional device (basic common points), but is different from the conventional one, in that across-body direction cross-sectional shapes of the solenoid coil 17 and the hollow frame 16 are D-shaped (the first difference). Compared with the body heating device 10, the body heating device 110 shares the common points and the first difference, thus becomes suitable for partial thermotherapy as for bladder cancer or the like, however, the secondary solenoid coil 21 of the second difference and the solid magnetic core 40 of the third difference do not exist in the device 110.

Regarding the body heating device 110 of the second embodiment, use and operation thereof will be described referring to the attached drawings. FIG. 4(*d*) is an along-bodyheight direction sectional view schematic block diagram showing a state in which the magnetic flux is irradiated to the patient 8 (the body, the body to be irradiated) (sectioned along the solenoid axial direction).

Also in this case, at first, the patient 8 in whom fine particles of the magnetic-sensitive heat-generating material are injected is laid on the movable bed 15 so that the affected area 8a is directed upward; for example, if the affected area 8a is in a lumbar part, the patient is laid on his stomach. Then, maintaining this state, the movable bed 15 is moved to send the patient 8 into the hollow frame 16 namely into the hollow part of the solenoid coil 17. Then the high-frequency power supply 11 is operated with a timing the magnetic-sensitive heat-generating material is deposited on the affected area, and the magnetic flux 9 extends in the axial direction of the solenoid coil 17, i.e. the body-height direction of the patient 8. At this time, the output of the high-frequency power supply 11 is adjusted so that the magnetic flux 9 is dense enough to treat the affected area 8a, and a coil current (and therefore a magnetic flux density) same as a conventional device is provided, but with an output voltage lower than the conventional device.

That is to say that, coil current and magnetic flux density enlarged than the conventional device can be provided with the same output voltage, and this effect is remarkable. This is because the impedance of the solenoid coil 17 decreases at the same number of coiling turn as the plain circular coil of the conventional device, with the modification of the coil shape to the shape having straight-lined part 17b. For example, in the case that a frequency of the alternating magnetic flux is 50 to 400 kHz suitable to generate magnetic hysteresis loss in the magnetic-sensitive heat-generating material, and electric current is about 200 A is fed to the solenoid coil 17, inductance of 20 μH in the conventional device decreases to about 15 μH, and accordingly the output voltage of the high-frequency power supply 11 lowers from 15 to about 10 kV.

Figure 5:
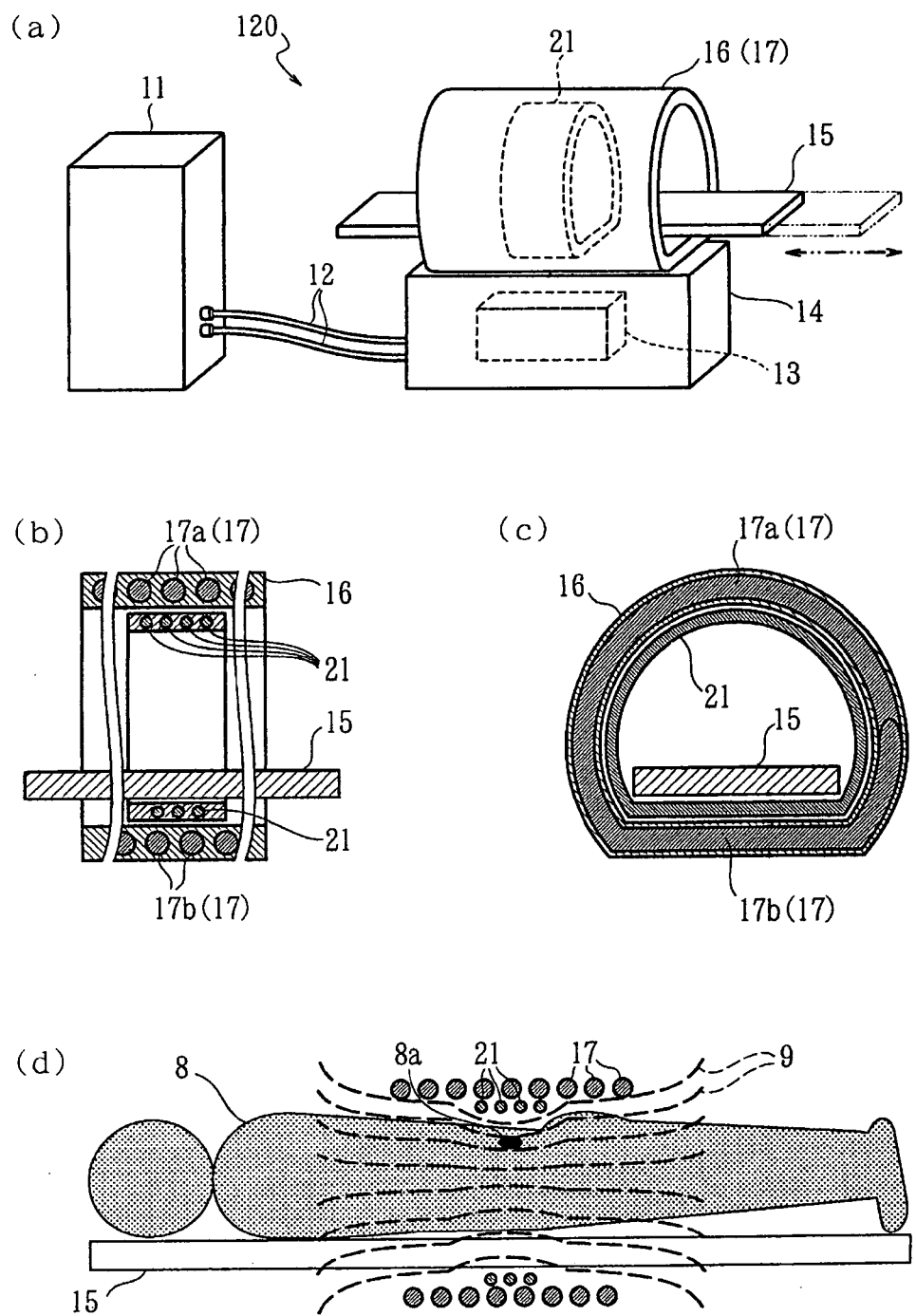
FIG. 5 illustrates a structure and use of a body heating device of the other embodiment according to the present invention (a third embodiment), where

Regarding a third embodiment of the body heating device according to the present invention, the structure thereof will be described referring to the attached drawings. FIG. 5(*a*) is a perspective view of the body heating device 120, FIG. 5(*b*) is an along-bodyheight direction cross-sectional view of the magnetic flux irradiator, and FIG. 5(*c*) is an across-body direction cross-sectional view of the magnetic flux irradiator.

The body heating device 120 includes the mount 14, the movable bed 15, the hollow frame 16, the solenoid coil 17 and the high-frequency power supply 11 like the conventional device (basic common points), but is different in that the across-body direction cross section of the solenoid coil 17 and the hollow frame 16 is D-shaped (the first difference), and also a secondary solenoid coil 21 with D-shaped across-body direction cross section is added (the second difference). Compared with the body heating device 10, the body heating device 120 takes over the common points and the first difference, and is suitable for partial thermotherapy for bladder cancer or the like, but the solid magnetic core 40 of the third difference do not exist in the device 120. Also, the difference between the body heating device 110 and the body heating device 120 is that the secondary solenoid coil 21 of the second difference is added in the body heating device 120.

Regarding the body heating device 120 of the third embodiment of the present invention, use and operation thereof will be described referring to the attached drawings. FIG. 5(*d*) is an along-bodyheight direction cross-sectional schematic view showing the state in which the magnetic flux is irradiated to the patient 8.

The process, in which the patient 8 with the magnetic-sensitive heat-generating material injected is laid on the movable bed 15 directing the affected area 8a upward, then sent into the hollow part of the solenoid coil 17, and the high-frequency power supply 11 is operated is the same as the process of the body heating device 110, but in this case, the movable bed 15 is stopped in a position where the affected area 8a is in the secondary solenoid coil 21. By doing this, the magnetic field generated by the secondary solenoid coil 21 is superposed on the magnetic field generated by the solenoid coil 17, and the magnetic flux 9 extending in the body-height direction of the patient 8 concentrates on the affected area 8a, resulting in denser flux.

In addition, by adding the secondary solenoid coil 21, the total winding number of coils including the solenoid coil 17 increases, and the amount of coil current required to generate an expected density of the magnetic flux 9 on the affected area 8a can be decreased. Therefore, even if the solenoid coil 17 and the secondary solenoid coil 21 are connected in series, in many cases output voltage increase of the high-frequency power supply 11 is not required. In some cases, output voltage of the high-frequency power supply 11 can be even decreased by a cooperation of the focus effect of the magnetic flux 9 due to the secondary solenoid coil 21 and an impedance reduction effect due to the modification of the solenoid coil 17 to the shape having the straight-lined part 17b.

As an example taking no account of output-voltage fluctuation often caused, for generating 300 mT (milli Tesla) of the magnetic flux 9, suitable for the heat-generating function of the magnetic-sensitive heat-generating material, on the affected area 8a, the output voltage required to the conventional device is about 20 kV whereas the output voltage required to the high-frequency power supply 11 of the body heating device 120 is about 10 kV.

Figure 6:
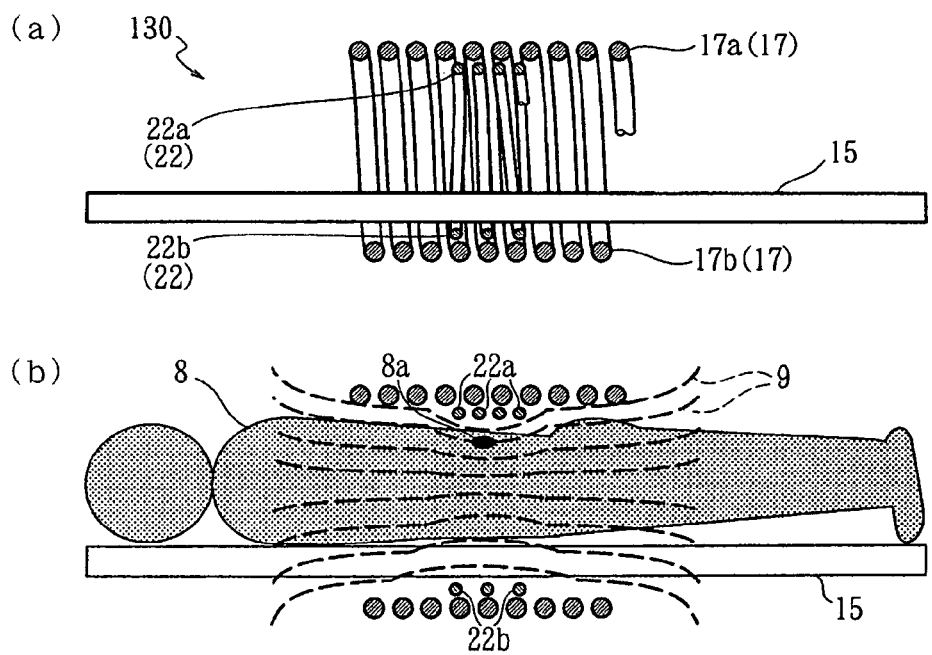
FIG. 6 illustrates a structure and use of a body heating device of the other embodiment according to the present invention (a fourth embodiment), where

Regarding a fourth embodiment of the body heating device according to the present invention, the structure thereof will be described referring to the attached drawings. FIG. 6(*a*) is an along-bodyheight direction cross-sectional view of the solenoid coil 17, the secondary solenoid coil 22 and the movable bed 15.

A difference between the body heating device 130 and the body heating device 120 is that the secondary solenoid coil 21 is partially modified, thus changed to the secondary solenoid coil 22. A difference between the secondary solenoid coil 21 and the secondary solenoid coil 22 is that the coiling pitch of the movable bed 15 biased side extends, for example, two times while maintaining the across-body direction cross-sectional shape as D-shaped, and in the secondary solenoid coil 22, the downward part of the movable bed 15 becomes the sparsely coiled part 22b. The upper part of the movable bed 15 in the secondary solenoid coil 22 referred as the part 22a coiled more densely than the solenoid coil 17 without modification.

Regarding the body heating device 130 of the fourth embodiment of the present invention, use and operation thereof will be described referring to the attached drawings. FIG. 6(*b*) is an along-bodyheight direction cross-sectional schematic view showing the state in which the magnetic flux is irradiated to the patient 8.

In this case, the magnetic flux 9 concentrates, as in the body heating device 120, on the affected area 8a near the densely coiled part 22a, but the magnetic flux 9 disperses more than in the case of the body heating device 120 in normal parts in the patient's body located beside the sparsely coiled part 22b, and the load on the normal parts decreases. Except these points, the body heating device 130 is alike the body heating device 120.

Figure 7:
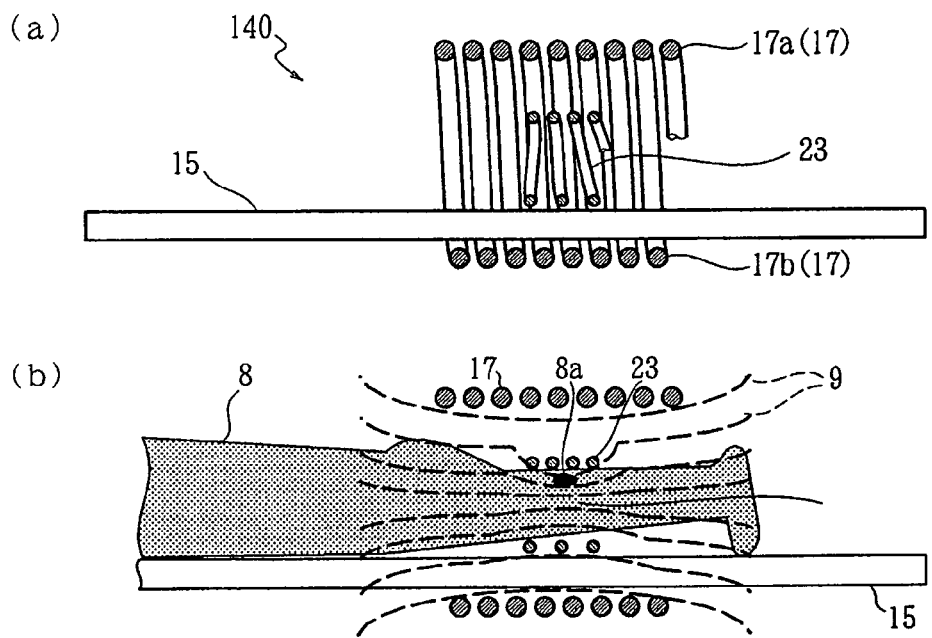
FIG. 7 illustrates a structure and use of a body heating device of the other embodiment according to the present invention (a fifth embodiment), where

Regarding a fifth embodiment of the body heating device according to the present invention, the structure thereof will be described referring to the attached drawings. FIG. 7(a) is an along-bodyheight direction cross-sectional view of the solenoid coil 17, the secondary solenoid coil 23 and the movable bed 15.

A difference between the body heating device 140 and the body heating device 130 is that the secondary solenoid coil 22 is changed to the secondary solenoid coil 23, which is thinner than the coil 22, decreasing its diameter, as the coil 23 becomes thinner-diametered while maintaining the across-body direction cross-sectional shape as D-shaped, the coil 23 is removed from the movable bed 15, and the feeding cable is flexible so that the coil 23 is movable anywhere within the hollow part of the solenoid coil 17. The secondary solenoid coil 23 can be inserted in and removed from the solenoid coil 17 freely, therefore, a switch or the like for switching the feeding circuit either only to the solenoid coil 17 or both to the solenoid coil 17 and the secondary solenoid coil 23 is provided so that electric feeding to the coil 23 can be cut-off removing the coil 23 from the solenoid coil 17. Alternatively, a totalized attachment system in which the secondary solenoid coil 23 can be inserted or removed, together with plugging on-or-off etc. of power line, can be provided.

Regarding the body heating device 140 of the fifth embodiment of the present invention, use and operation thereof will be described referring to the attached drawings. FIG. 7(b) is an along-bodyheight direction cross-sectional schematic view showing the state in which the magnetic flux is irradiated to the patient 8.

In the case that the affected area 8a is a foot or a hand, the secondary solenoid coil 23 is fit on the foot or hand surrounding the affected area 8a, the movable bed 15 is stopped where the affected area 8a and the secondary solenoid coil 23 enter in the hollow part of the solenoid coil 17, then the magnetic flux 9 is generated as in the devices 120 and 130 except above points, and so the magnetic flux 9 is irradiated intensively to the affected area 8a.

In the case that the affected area 8a is located in the torso, the secondary solenoid coil 23 is removed from the solenoid coil 17 and the power is stopped to the secondary solenoid coil 23 and fed only to the solenoid coil 17, thus the magnetic flux irradiation is performed as in the body heating device 110.

Figure 8:
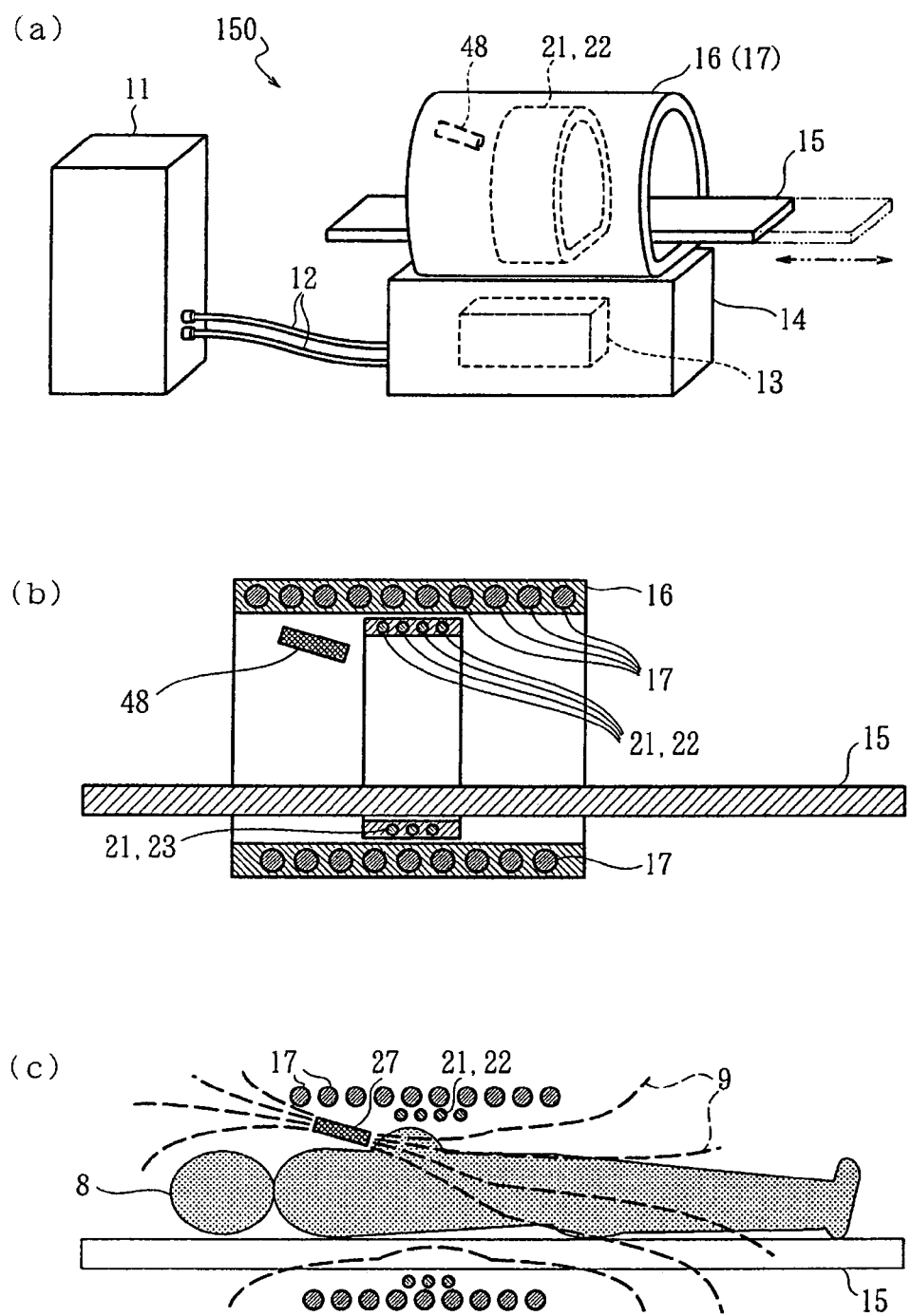
FIG. 8 illustrates a structure and use of a body heating device of the other embodiment according to the present invention (a sixth embodiment), where

Regarding a sixth embodiment of the body heating device according to the present invention, the structure thereof will be described referring to the attached drawings. FIG. 8(a) is a perspective view of the body heating device 150 and FIG. 8(b) is an along-bodyheight direction cross-sectional view of the magnetic flux irradiator.

The body heating device 150 is suitable for partial thermotherapy such as breast cancer. A difference between the body heating device 150 and the body heating device 120 and 130 is that the magnetic core 48 which can be easily inserted in the hollow part of the solenoid coil 17 is added (the third difference). Compared with the body heating device 10, the body heating device 150 takes over aforesaid common points and the first to third differences, but a concrete aspect of the third difference is changed, i.e. the magnetic core 48 is employed instead of the magnetic core 40.

The magnetic core 48 includes a ferromagnetic core such as sintering ferrite-oxide, and formed into a bar shape (stick-shape, straight-line shape, straight-bar shape) in this embodiment. The magnetic core 48 is to concentrate the magnetic flux on the affected area in the hollow part of the solenoid coil 17, and its size and a shape is set up corresponding to the affected area. For example, the magnetic core for breast cancer has a diameter of several centimeters, and a length of several tens of centimeters with a round-bar shape. Further, depending on the affected area shape, the magnetic core may be L-shaped, crescent-moon shaped or the like.

Regarding the body heating device 150 of the sixth embodiment of the present invention, use and operation thereof will be described referring to the attached drawings. FIG. 8(c) is an along-bodyheight direction cross-sectional schematic view showing in the case that magnetic flux is irradiated to the patient 8.

As already described, also in this case the patient 8 in whom fine particles of the magnetic-sensitive heat-generating material are injected is laid on the movable bed 15, then one end of the magnetic core 48 acting as the working end is directed to the affected area. While maintaining this state, the movable bed 15 is moved to send the patient 8 into the hollow frame 16 namely into the hollow part of the solenoid coil 17. The movable bed 15 is stopped where the affected area enters the hollow parts of the secondary solenoid coil 21 or 22. By operating the high-frequency power supply 11 with a timing that the magnetic-sensitive heat-generating material deposited on the affected area the magnetic flux 9 extending in the axial direction of the solenoid coil 17, i.e. the body-height direction of the patient 8 is generated. While the magnetic flux 9 concentrates on the secondary solenoid coils 21 or 22 entirely and generally, concentrates on the magnetic core 48 strongly, and is irradiated densely on the affected area. On parts other than the above, the magnetic flux 9 extends to both ends of the solenoid coil 17 while diffusing and dispersing in the radial direction in the hollow part of the solenoid coil 17.

For example, even in the case that 300 mT (milli Tesla) of the magnetic flux suitable for the heat generating function of the magnetic-sensitive heat-generating material are irradiated on the affected area, only about 10 to 100 mT of the magnetic flux is irradiated on other areas of the body. So, in the situation that the high-frequency alternating magnetic flux of 50 to 400 kHz suitable to generate magnetic hysteresis loss in the magnetic-sensitive heat-generating material being applied, normal body areas including body surface are not heated undesirably.

Thus, in the body heating device 150, the high density magnetic flux is irradiated on the affected area such as breast cancer, i.e. a limited area of the body is heated sufficiently with no side effects to the patient 8.

Regarding a seventh embodiment of the body heating device according to the present invention, the structure thereof will be described referring to the attached drawings. FIG. 9(a) is a perspective view of the body heating device 160 and FIG. 9(b) is an along-bodyheight direction cross-sectional view of the magnetic flux irradiator.

The difference between the body heating device 160 and the body heating device 150 is that the main solenoid coil and the secondary solenoid coil do not have an across-body direction cross-sectional shape as D-shaped but have a cross-sectional shape as plain circular-shaped.

In other words, the body heating device 160 includes the same mount 14, movable bed 15, hollow frame 18, main solenoid coil 19 and high-frequency power supply 11 of the conventional device (basic common points), but is different from the conventional one in that the secondary solenoid coil 24 (the second difference) and the magnetic core 48 (the third difference) are added. The first difference is not adopted in the device 160, and across-body direction cross-sectional shapes of the hollow frame 18 and the solenoid coil 19 are not of D-shaped but of plain circle like the conventional one. Accordingly, the secondary solenoid coil 24 has a plain circular shape by modifying the secondary solenoid coil 21 or 22.

The magnetic core 48 is a bar shaped ferromagnetic core.

Figure 9:
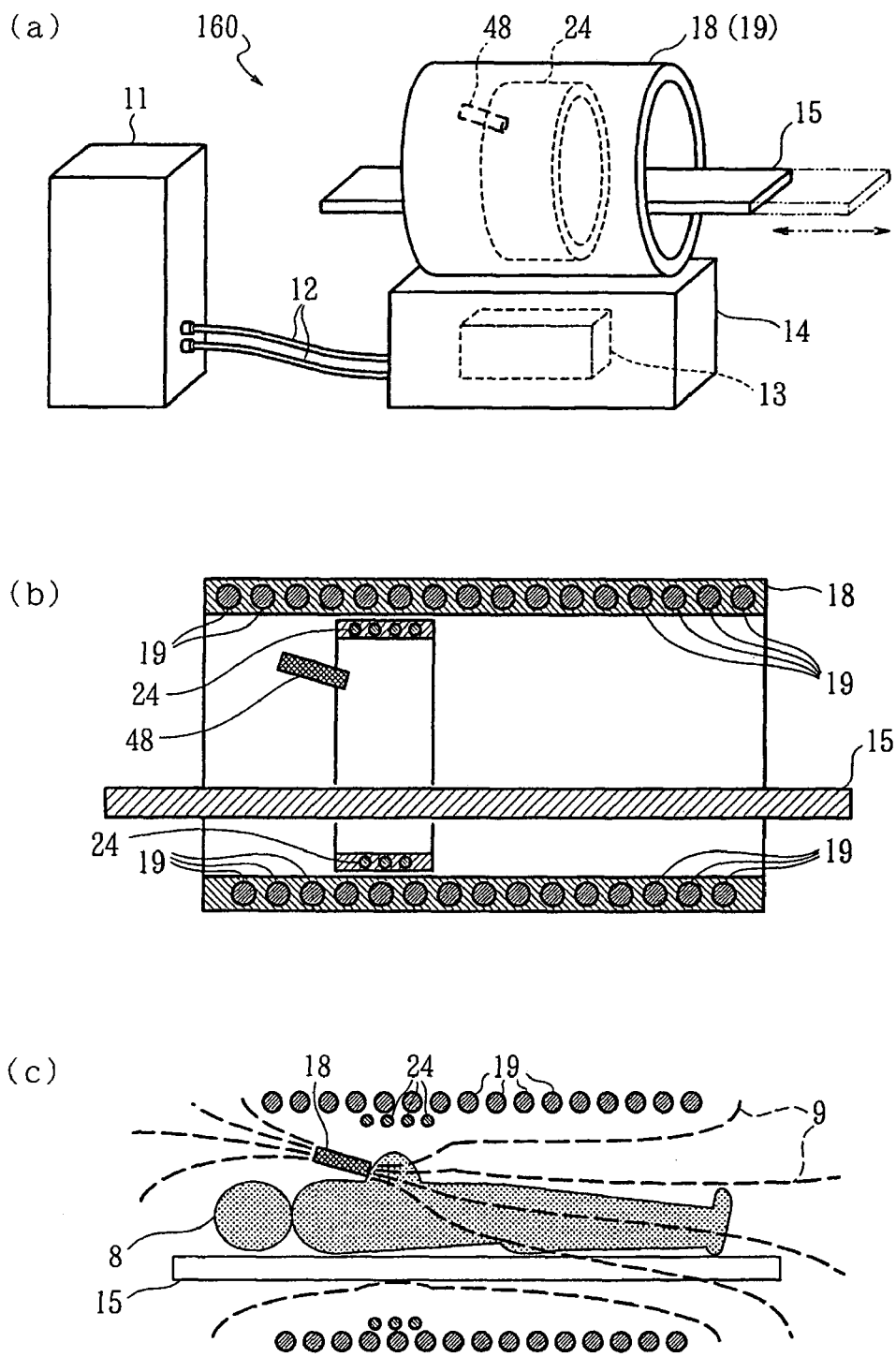
FIG. 9 illustrates a structure and use of a body heating device of the other embodiment according to the present invention (a seventh embodiment), where

Regarding the body heating device 160 of the seventh embodiment of the present invention, use and operation thereof will be described referring to the attached drawings. FIG. 9(*c*) is an along-bodyheight direction cross-sectional schematic view showing in the case that magnetic flux is irradiated to the patient 8.

The only difference of the solenoid coil 19 and the secondary solenoid coil 24 in the device 160 from the coils 17, 21 or 22 in the body heating device 150 is their across-body direction cross-sectional shape, so the use of the body heating device 160 may be the same of the body heating device 150. As the redundant description is omitted, regarding working effect, the effect of the point, as the across-body direction cross-sectional D-shaped of the solenoid coil 19 cannot be obtained, but the effect of the secondary solenoid coil 24 and the effect of the magnetic core 48 are both obtained.

Figure 10:
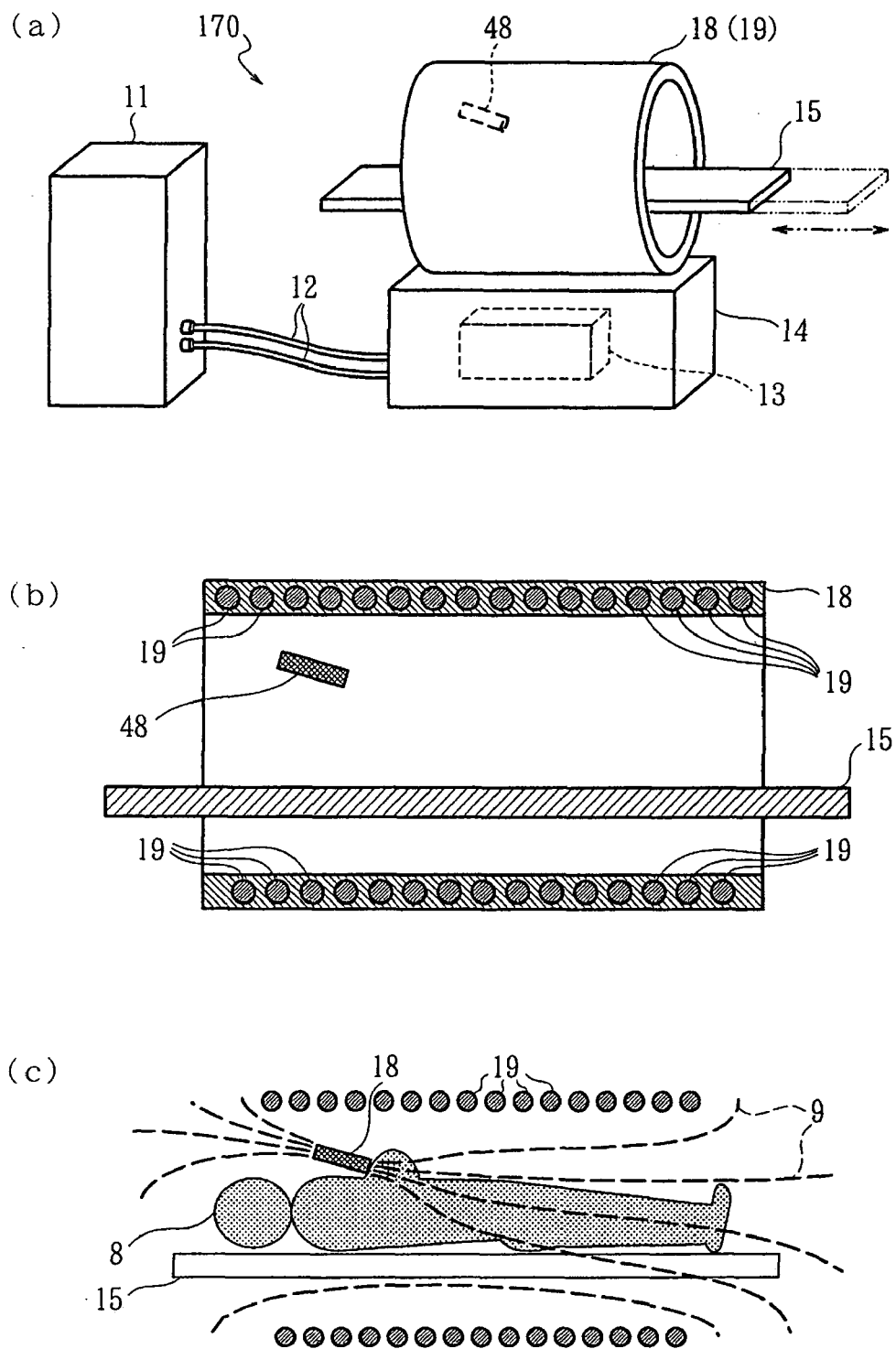
FIG. 10 illustrates a structure and use of a body heating device of the other embodiment according to the present invention (an eighth embodiment), where

Regarding an eighth embodiment of the body heating device according to the present invention, the structure thereof will be described referring to the attached drawings. FIG. 10(*a*) is a perspective view of the body heating device 170 and FIG. 10(*b*) is an along-bodyheight direction cross-sectional view of the magnetic flux irradiator.

The difference between the body heating device 170 and the body heating device 160 is the omission of the secondary solenoid coil 24.

In other words, the body heating device 170 includes the same mount 14, movable bed 15, hollow frame 18, main solenoid coil 19 and high-frequency power supply 11 of the conventional device (basic common points), but is different from the conventional one in that the magnetic core 48 is added (the third difference). Further, the first difference is not employed, thus the across-body direction cross-sectional shape of the solenoid coil 17 and the hollow frame 16 are not of D-shaped, but plain circular like the conventional device. In addition, the secondary solenoid coil, which is the second difference, is not adopted.

The magnetic core 48 is a ferromagnetic core with a bar shape.

Regarding the body heating device 170 of the eighth embodiment of the present invention, use and operation thereof will be described referring to the attached drawings. FIG. 10(*c*) is an along-bodyheight direction cross-sectional schematic view showing in the case that magnetic flux is irradiated to the patient 8.

As already described, the patient 8 in whom fine particles of the magnetic-sensitive heat-generating material are injected is laid on the movable bed 15, then one end acting as working end of the magnetic core 48 is directed to the affected area, and while maintaining this state, the movable bed 15 is moved to send the patient 8 into the hollow frame 18 namely into the hollow part of the solenoid coil 19. By operating the high-frequency power supply 11 with a timing that the magnetic-sensitive heat-generating material deposited on the affected area, the magnetic flux 9 is generated extending in the axial direction of the solenoid coil 19, i.e. the body-height direction of the patient 8. The magnetic flux 9 converges in the magnetic core 48 and irradiates the affected area densely. On the other hand, in parts other than the magnetic core 48, the magnetic flux 9 extends to both ends of the solenoid coil 19, diffusing and dispersing to the radial direction of the hollow part of the solenoid coil 19.

Therefore, for example, even if 300 mT (milli Tesla) of the magnetic flux suitable for the heating function of the magnetic-sensitive heat-generating material are irradiated on the affected area, only about 10 to 100 mT of the magnetic flux is irradiated on the body other than the affected area, so, in the situation that the high-frequency alternating magnetic flux of 50 to 400 kHz suitable to generate magnetic hysteresis loss in the magnetic-sensitive heat-generating material being applied, normal body areas including body surface are not heated undesirably.

Thus, with the body heating device 170, a magnetic flux of high density is irradiated on the affected area such as breast cancer, i.e. a limited area of the body is heated sufficiently with no side effects to the patient 8.

Figure 11:
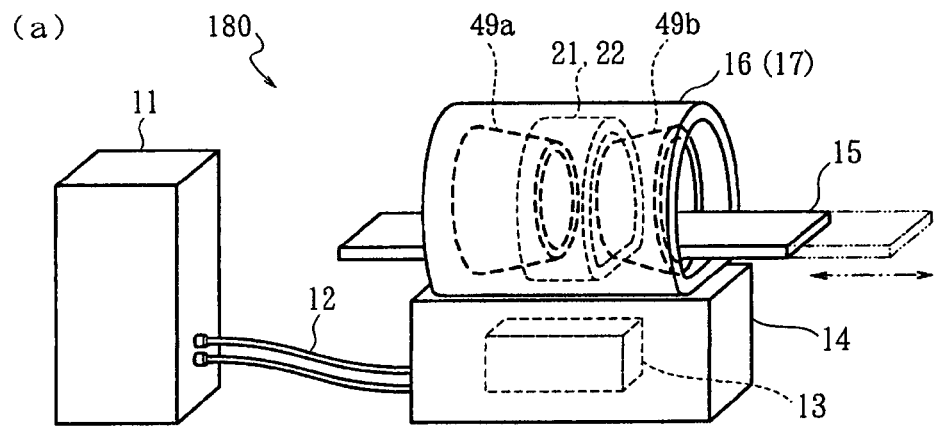
FIG. 11 illustrates a structure and use of a body heating device of the other embodiment according to the present invention (a ninth embodiment), where
Figure 11:
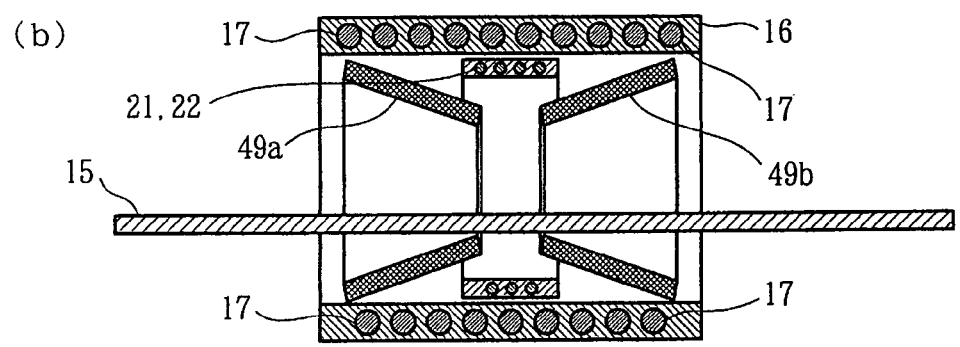
Figure 11:
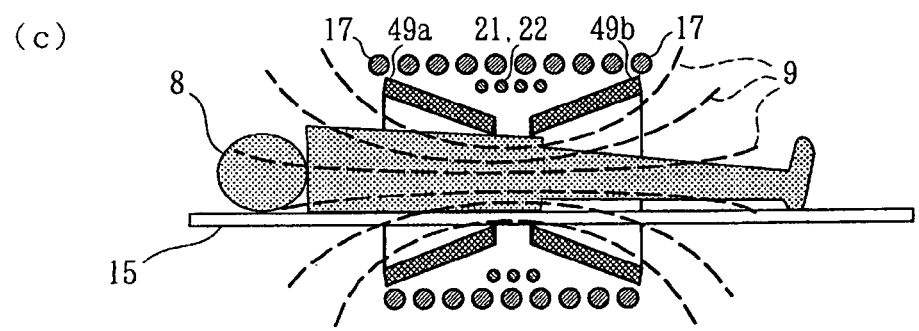

Regarding a ninth embodiment of the body heating device of the present invention, the structure thereof will be described referring to the attached drawings. FIG. 11(*a*) is a perspective view of the body heating device 180 and FIG. 11(*b*) is an along-bodyheight direction cross-sectional view of the magnetic flux irradiator.

The difference between the body heating device 180 and the body heating device 150 is that the single magnetic core 48 is changed to a plurality of the magnetic cores 49*a* and 49*b* for irradiation of magnetic flux to deep affected areas, and the magnetic cores are separated in an axial direction of the solenoid coil 17. The magnetic cores 49*a* and 49*b* both include the ferromagnetic material such as sintering ferrite-oxide, and are cylindrical cores having a diameter varied in a tapered shape. However, the magnetic cores have a diameter smaller than the hollow frame 16 and a length less than half of the length of the frame 16. Therefore, the magnetic cores can be easily inserted in the hollow part of the hollow frame 16 arranging separately in the axial direction. Though they are thinner than the hollow frame 16, they are thick enough to be inserted in the movable bed 15.

Regarding the body heating device 180 of the ninth embodiment of the present invention, use and operation thereof will be described referring to the attached drawings. FIG. 11(*c*) is an along-bodyheight direction cross-sectional schematic view showing state in which the magnetic flux is irradiated to the patient 8.

Regarding bladder or internal organ cancer, the affected area is in deep areas at the abdomen or the chest of the patient 8, so the density of the magnetic flux is increased by arranging the magnetic cores 49*a* and 49*b* as each thin-diametered end thereof is faced each other, thus collecting the magnetic flux between the thin-diametered ends. As already described, the patient 8 in whom fine particles of magnetic-sensitive heat-generating material are injected is laid on the movable bed 15. Then the secondary solenoid coil 21 or 22 is fixed to the movable bed 15, positioning the secondary solenoid coil 21 or 22 as the affected area enters the hollow part of the secondary solenoid coil 21 or 22. Thereafter, for example, the left magnetic core 49*a* is arranged as a thick-diametered end thereof on the left and a large-diametered end thereof on the right, and the magnetic core 49*a* is engaged with the movable bed 15 and the patient 8 from the left side, on the other hand, the right magnetic core 49*b* is arranged as a large-diametered end thereof on the right and a small-diametered end thereof on the left, and the magnetic core 49*b* is engaged with the movable bed 15 and the patient 8 from the right side, then the positions of the magnetic cores 49*a* and 49*b* are fixed relatively to the movable bed 15, as the secondary solenoid coil 21 or 22, and the affected area of the patient 8 is located at the intermediate place between the magnetic cores 49*a* and 49*b*.

The relative position between the patient 8 and the secondary solenoid coil 21 or 22 and the magnetic cores 49*a* and 49*b* is also fixed, as the above, then, while maintaining this state, the movable bed 15 is moved to send the patient 8 into the hollow frame 16 namely into the hollow part of the solenoid coil 17. Also in this case, by operating the high-frequency power supply 11 with a timing that the magnetic-sensitive heat-generating material deposited on the affected area, a magnetic flux 9 is generated extending in the axial direction of the solenoid coil 17, i.e. the body-height direction of the patient 8. The magnetic flux 9 converges in the secondary solenoid coil 21 or 22, i.e. between the thin-diametered ends of the magnetic cores 49a and 49b, then is irradiated densely to a deep abdominal part of the patient 8. On the other hand, at the thick-diametered end of the magnetic cores 49a and 49b and also outside thereof, the magnetic flux 9 extends to both ends of the solenoid coil 17 while diffusing and dispersing in the hollow part of the solenoid coil 17 in the radial direction.

Also in the body heating device 180 the magnetic flux of high density is irradiated on the affected area such as internal organ cancer, i.e. a limited area of the body is heated sufficiently with no side effects to the patient 8.

As shapes of the magnetic cores 49a and 49b, a taper-shaped cylindrical core is illustrated, however, the shape may be an across-body direction cross-sectionally as D-shaped like the secondary solenoid coils 21 or 22. Concretely, the movable bed 15 biased side of the cores may be modified to a plane shape parallel to the movable bed 15 for example.

A structure without the secondary solenoid coils 21 or 22, and a structure with plane circular the solenoid coil 19 instead of the D-shaped solenoid coil 17, can also serve.

Figure 12:
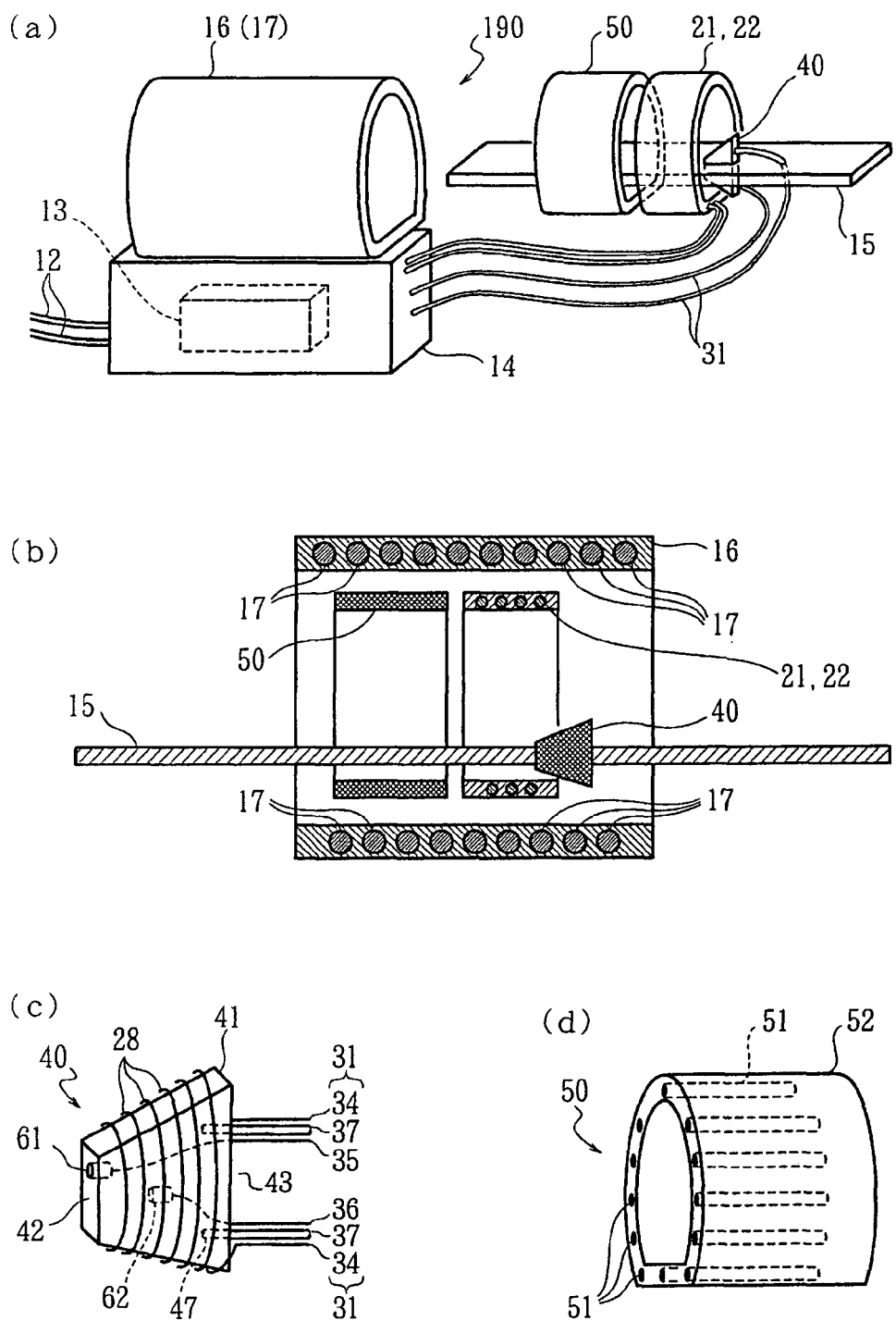
FIG. 12 illustrates a structure and use of a body heating device of the other embodiment according to the present invention (a tenth embodiment), where
Figure 13:
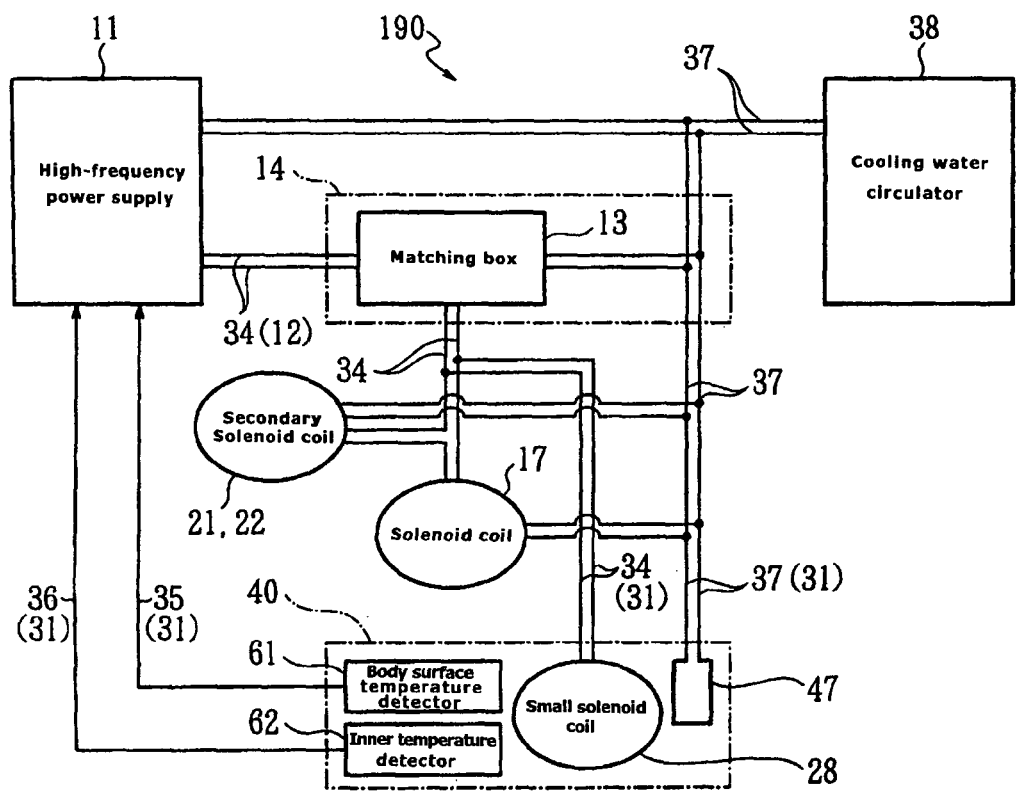
FIG. 13 is a circuit block diagram of the body heating device of the tenth embodiment.

Regarding a tenth embodiment of the body heating device of the present invention, the structure thereof will be described referring to the attached drawings. FIG. 12(*a*) is a perspective view of the body heating device 190, FIG. 12(*b*) is an along-bodyheight direction cross-sectional view of the magnetic flux irradiator, FIG. 12(*c*) is a perspective view of a solid magnetic core 40, and FIG. 12(*d*) is a perspective view of a hollow magnetic core 50. FIG. 13 is a circuit block diagram of the body heating device 190.

A difference of the body heating device 190 from the body heating device 180 (refer to FIGS. 12(*a*) and 12(*b*)), is that the magnetic core 49b at the side of the lower part of the body is changed to the solid magnetic core 40 for converging the magnetic flux to target prostate cancer, and the magnetic core 49a of the side of the upper part of the body is changed to the hollow magnetic core 50 for diffusing the magnetic flux to minimize magnetic action to the head and chest.

The hollow magnetic core 50 is installed onto the movable bed 15 so that the movable bed 15 is inserted in a hollow part of the magnetic core 50 and the magnetic core 50 can be moved relatively in the axial direction thereof, i.e. the along-bodyheight direction of the movable bed 15. The solid magnetic core 40 is fixed to the movable bed 15 being plugged in and a portion thereof being protruded upwardly from the movable bed 15 then connected to the mount 14 by the cable 31. The secondary solenoid coil 21 or 22 is installed so as to be moved to a intermediate place between the hollow magnetic core 50 and the solid magnetic core 40, and then fixed.

The solid magnetic core 40 (refer to FIG. 12(*c*)) mainly includes the core-body 41 with the body surface temperature detector 61 like the body heating device 10. The core-body 41 is installed on the movable bed 15 so that the working end 42 is directed to the affected area. In the solid magnetic core 40 of the present embodiment, the small solenoid coil 28 is coiled on the core-body 41, to reinforce the magnetic flux penetrating through the working end 42 and the non-working end 43 of the core-body 41 to a higher level than the magnetic flux in the body heating device 10. The small solenoid coil 28 is connected to the matching box 13 with the high-frequency power line 34 in the cable 31 (refer to FIG. 13), and driven with a high-frequency current fed from the high-frequency power supply 11 together with the solenoid coil 17 and the secondary solenoid coil 21 or 22.

The core-body 41 (refer to FIG. 12(*c*)) has, for example, an inner temperature detector 62 with a built-in semiconductor sensor embedded in the core-body 41 to detect temperature of the core-body 41. The inner temperature detector 62 (refer to FIG. 13) is also connected to the high-frequency power supply 11 with the signal line 36 in the cable 31 so as to use the detected temperature thereof to control of high-frequency power. For example, in the case that the magnetic susceptibility of the solid magnetic core 40 is undesirably decreased in the case that the temperature detected by the inner temperature detector 62 exceeds 100° C. which is a reference temperature, in relation with the magnetic transition temperature, the output of the high-frequency power supply 11 is decreased from the reference temperature to prevent the decreasing of the magnetic permeability.

The core-body 41 (refer to FIG. 12(*c*)) has a magnetic core cooling means for compulsive cooling. Concretely, the coolant flow path 47 for forced cooling is formed going around and U-turning in the core-body 41 so for example. The coolant flow path 47 is connected to a cooling water circulator 38 with a flexible piping 37 in the cable 31 (refer to FIG. 13). Thus the solid magnetic core 40 is also constituted so as to be cooled by water like the matching box 13, the solenoid coil 17, and the secondary solenoid coils 21 or 22.

The hollow magnetic core 50 (refer to FIG. 12(*d*)) is cylindrical and includes ferromagnetic material like the magnetic core 49a, and constituted so as to have an outer diameter smaller than the inner diameter of the hollow frame 16 and an inner diameter larger than the breadth of the movable bed 15, so the hollow magnetic core 50 can be easily inserted between the movable bed 15 and the hollow frame 16 (refer to FIGS. 12(*a*), 12(*b*)). The hollow magnetic core 50 has a length half or shorter than the hollow frame 16 and an axial line thereof is parallel to the axial line of the solenoid coil 17. The solid magnetic core 40 and the hollow magnetic core 50 are arranged separately in the solenoid coil 17. The hollow magnetic core 50 may has a tapered cylindrical shape changing the diameter along the axial line, like the magnetic core 49a, and as it is sufficient to perform the magnetic flux dispersing function, thus, in this embodiment, it has the cylindrical shape with the same diameter over the total length.

The production cost increases if the hollow magnetic core 50 with a large diameter is made solidly of the ferromagnetic material, therefore, as the practical hollow magnetic core 50 (refer to FIG. 12(*d*)), for example, a plurality of bar shaped magnetic core-body 51 arranged circumferentially, being molded with plastic matrix in a hollow frame 52, may be used. Further, instead of said plastic molding, the belt-shaped elastic article equipped with the plurality of core-body 51, or a rubber-based or soft-plastic-based article having belt-shape in which ferromagnetic particles are kneaded-in is also useful because it can be installed by fitting to the body. The hollow magnetic core 50 also has an across-body direction cross-sectional shape as D-shaped with a flat bottom like the solenoid coil 17 and the secondary solenoid coil 21 or 22.

Figure 14:
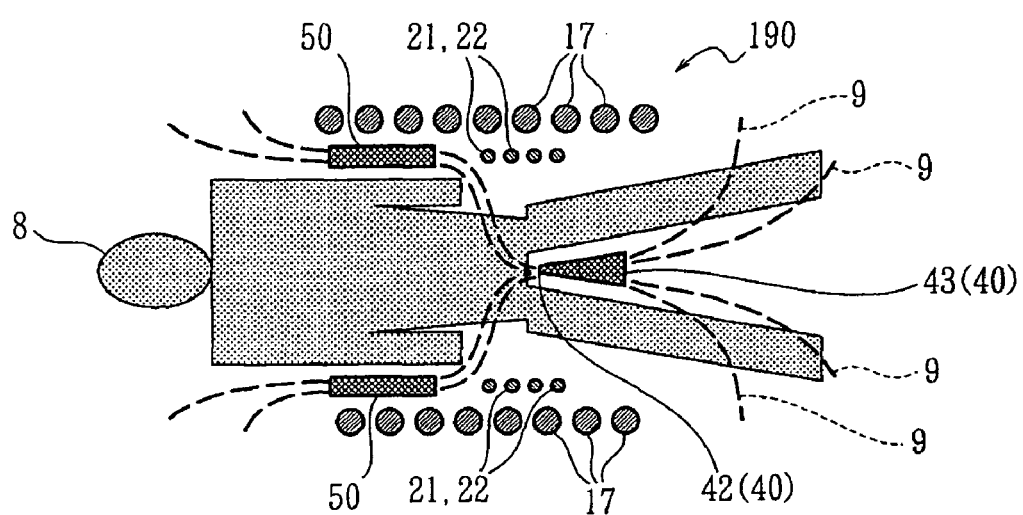
FIG. 14 is a plane-viewed along-bodyheight direction cross-sectional schematic view (sectioned along the solenoid axial direction) illustrating a use of the body heating device in the case that the magnetic flux irradiator irradiates the magnetic flux.

Regarding the body heating device 190 of the tenth embodiment of the present invention, use and operation thereof will be described referring to the attached drawings. FIG. 14 is a plane viewed along-bodyheight direction cross-sectional schematic view (sectioned along the solenoid axial direction) showing the body heating device irradiating the magnetic flux to the patient 8. Here, prostate cancer of the patient 8 is treated with partial thermotherapy.

As already described, the patient 8 in whom fine particles of magnetic-sensitive heat-generating material are injected is laid on the movable bed 15, but in this case the solid magnetic core 40 can be set between the patient 8's thighs at the root thereof, directing the working end 42 to the abdomen of the patient 8 and the non-working end 43 to the tiptoes of the patient 8. Then, the secondary solenoid coil 21 or 22 is slid in the along-bodyheight direction of the movable bed 15 and the secondary solenoid coil 21 or 22 is located at a part surrounding the affected area of the patient 8. Then, the hollow magnetic core 50 is slid in the along-bodyheight direction of the movable bed 15 so that the hollow magnetic core 50 surrounds the chest of the patient 8. As a result, each position of the solid magnetic core 40, the secondary solenoid coil 21 or 22, hollow magnetic core 50, and the patient 8 is fixed based on the movable bed 15, and while maintaining this state, the movable bed 15 is moved to send the patient 8 into the hollow frame 16 namely into the hollow part of the solenoid coil 17.

By operating the high-frequency power supply 11 with a timing that the magnetic-sensitive heat-generating material deposited on the affected area, the magnetic flux 9 is generated and extends in the axial direction of the solenoid coil 17, i.e. the body-height direction of the patient 8, as the summarized state in the whole area of the hollow part of the hollow frame 16 surrounding the patient 8 also in this case. The magnetic flux 9 extends to both ends of the solenoid coil 17, concentrating entirely and generally in the secondary solenoid coils 21 or 22, and besides, not only converging in the core-body 41 of the solid magnetic core 40 but also further reinforced by the small solenoid coil 28, then irradiated densely to the affected area in the inner area of the body, on the other hand, in the solenoid coil 17, immediately diffusing and dispersing in the radial direction of the hollow magnetic core 50, and at a point (right in the drawing) of the non-working end 43 of the solid magnetic core 40, moderately diffusing and dispersing.

In the solid magnetic core 40, heat is generated from the core-body 41 by the alternating magnetic field of the small solenoid coil 28 and the heat is removed with from the cooling water from the circulator 38, but in the case that the generated heat exceeds removed heat, undesirable temperature-rising of the core-body 41, is detected by the inner temperature detector 62, and depending on the detection, the output of the high-frequency power supply 11 is suppressively adjusted, thereby the magnetic flux converging capability and the magnetic flux reinforcement ability of the solid magnetic core 40 are maintained adequately. Also, in the case that the temperature of the patient 8's perineum undesirably, it is detected by the body surface temperature detector 61, and depending on the detection, the output of the high-frequency power supply 11 is suppressively adjusted, so that the normal body surface of the patient 8 is not heated undesirably even if near the affected area.

Of course, regarding a body surface apart from the affected area, the magnetic flux penetrating therethrough diffuses or disperses and the gradient of the magnetic flux density is small, and so is the amount of current induced by the alternating magnetic field, the result is that said surface is not heated undesirably.

Therefore, in the body heating device 190, the magnetic flux of high density is irradiated on the affected area such as prostate cancer, thus only a limited area of the body is to be heated sufficiently with no side effects to the patient 8.

Others

The above embodiments are structured so that the movable bed 15 moves sideward, but can be structured so that either the article such as the solenoid coil 17, 19, the secondary solenoid coil 21, 22 is to be moved, or both the movable bed 15 and said article is to be moved.

And, in the above embodiments the movable bed 15 is arranged horizontally together with said article, but can be arranged longitudinally or slantedly.

Further, the body holder is not limited to the movable bed 15 biased to the side of the cross-sectionally straight-lined part 17b of the solenoid coil 17. For example, a holder with a gutter on one face and fit with another face to the inner face of the arched part 17a of the solenoid coil 17 may be employed and the holder may be structured so that the patient 8 leans on the holder or can keep on standing with hand rail.

In the tenth embodiment, the detected result of the inner temperature detector 62 is used only for adjustment of the output from the high-frequency power supply 11, but can be used to adjust the temperature or the quantity of the water supplied from the cooling water circulator 38, or both uses can be adopted together.

In addition, the high-frequency power supply 11 is provided so that the electrical power is fed inclusively to the solenoid coil 17 and the secondary solenoid coils 21 or 22 and the small solenoid coil 28, from one high-frequency power supply, but can be constituted so that the electric power is fed to said solenoid coils from the plural high-frequency power supplies (or plural high-frequency output circuits equipped in one power supply) individually with synchronized phases; both the inclusive feeding and the individual feeding can be used together with various combination.

In the fifth embodiment, as the secondary solenoid coil 23 which can be inserted in and removed from the solenoid coil 17, has a shape small-sized from the secondary solenoid coil 22 with uneven coiling density, but the secondary solenoid coil 23 may have a shape small-sized from the secondary solenoid coil 21 with even coiling density, or small-sized from the secondary solenoid coil 24 not D-shaped at the cross-section of the across-body direction depending on the location of the affected area 8a, and so on.

INDUSTRIAL APPLICABILITY

Although the body heating device according to the present invention has been developed for treatment of human cancer, it is useful too, for other illness, in the case that the irradiation of magnetic flux is effective thereto, further it can also be used for other animals, for example pets.

The invention claimed is:

1. A body heating device comprising:
   a solenoid coil in which a living body is insertable;
   a high-frequency power supply to drive the solenoid coil;
   a movable bed which is insertable in the solenoid coil;
   wherein a cross section of the solenoid coil has an arched section and a straight section, and a secondary solenoid coil with shorter length and coiled more densely compared with the solenoid coil is arranged in the solenoid coil, and the driving power is fed from the above-mentioned or other high-frequency power supply to the secondary solenoid coil;
   a magnetic core which is insertable in the solenoid coil is further installed on the movable bed; and
   wherein the magnetic core is configured to concentrate magnetic flux on an affected area of the living body.

2. The body heating device according to claim 1, wherein a cross-sectional area of the magnetic core decreases toward a top, which is used as a working end.

3. The body heating device according to claim 2, wherein a body surface temperature detector for detecting a temperature on a body surface facing to the working end is installed on the working end of the magnetic core.

4. A body heating device comprising:
a solenoid coil in which a living body is insertable;
a high-frequency power supply to drive the solenoid coil;
a movable bed which is insertable in the solenoid coil;
wherein a cross section of the solenoid coil has an arched section above the movable bed and has a straight section under the movable bed;
wherein the movable bed is insertable in the solenoid coil when a living body is on the movable bed;
wherein the solenoid coil generates magnetic flux when applying current; and
wherein a secondary solenoid coil with shorter length and coiled more densely compared with the solenoid coil is arranged in the solenoid coil, and power is fed from the above-mentioned or other high-frequency power supply to the secondary solenoid coil.

5. The body heating device according to claim 4, wherein a coiling density of the secondary solenoid coil is densest at the side near the arched section of the solenoid coil and sparsest at the side near the straight section of the solenoid coil.

6. The body heating device according to claim 5, wherein the secondary solenoid coil is movable from the solenoid coil.

7. The body heating device according to claim 4, wherein the secondary solenoid coil is insertable in and movable from the solenoid coil.

8. The body heating device according to claim 4, wherein a magnetic core is insertable in the solenoid coil.

9. The body heating device according to claim 8, wherein a plurality of the magnetic core is separately disposed in the axial direction of the solenoid coil.

10. A body heating device comprising:
a solenoid coil in which a living body is insertable;
a high-frequency power supply to drive the solenoid coil;
a movable bed which is insertable in the solenoid coil;
wherein a cross section of the solenoid coil has an arched section above the movable bed and has a straight section under the movable bed;
wherein the movable bed is insertable in the solenoid coil when a living body is on the movable bed;
wherein the solenoid coil generates magnetic flux when applying current; and
wherein a magnetic core, which is insertable in the solenoid coil, is arranged in the solenoid coil.

11. The body heating device according to claim 10, wherein a plurality of the magnetic core is separately disposed in the axial direction of the solenoid coil.

12. The body heating device according to claim 11, wherein the magnetic core comprises a solid magnetic core for converging the magnetic flux and a hollow magnetic core for dispersing the magnetic flux.

13. The body heating device according to claim 12, wherein a cross-sectional area of the solid magnetic core decreases toward a top, which is used as a working end.

14. The body heating device according to claim 12, wherein the solid magnetic core is installed on the moveable bed.

15. The body heating device according to claim 12, wherein a body surface temperature detector for detecting a temperature on a body surface facing to the working end is installed on the working end of the solid magnetic core.

16. The body heating device according to claim 12, wherein an inner temperature detector is installed in the solid magnetic core for detecting an inner temperature thereof.

17. The body heating device according to claim 12, wherein the hollow magnetic core is a complex of a ferromagnetic material and a polymer.

18. The body heating device according to claim 12, wherein a small solenoid coil driven by the above-mentioned or other high-frequency power supply is coiled on the solid magnetic core.

19. The body heating device according to claim 18, further comprising magnetic core cooling means for cooling the solid magnetic core.

20. A body heating device comprising:
a solenoid coil in which a living body is insertable;
a high-frequency power supply to drive the solenoid coil;
a movable bed which is insertable in the solenoid coil; and
wherein a secondary solenoid coil with shorter length and coiled more densely compared with the solenoid coil is arranged in the solenoid coil, and power is fed from the above-mentioned, or other high-frequency power supply to the secondary solenoid coil.

21. The body heating device according to claim 20, wherein a magnetic core which is insertable in the solenoid coil is arranged.

22. The body heating device according to claim 21, wherein a plurality of the magnetic core is separately disposed in the axial direction of the solenoid coil.

23. A body heating device comprising:
a solenoid coil in which a living body is insertable;
a high-frequency power supply to drive the solenoid coil;
a movable bed which is insertable in the solenoid coil;
wherein a magnetic core which is insertable in the solenoid coil is arranged in the solenoid coil; and
wherein the magnetic core is configured to concentrate magnetic flux on an affected area of the living body.

24. The body heating device according to claim 23, wherein a plurality of the magnetic core is separately disposed in the axial direction of the solenoid coil.

* * * * *